(12) United States Patent
Doherty

(10) Patent No.: US 10,449,157 B2
(45) Date of Patent: Oct. 22, 2019

(54) PROCESS FOR PRODUCING MICROCAPSULES COMPRISING AN ACTIVE COMPONENT ENCAPSULATED, PROTECTED AND STABILISED WITHIN A PROTEIN SHELL

(71) Applicant: Anabio Technologies Limited, Dublin (IE)

(72) Inventor: Sinead Doherty, Dublin (IE)

(73) Assignee: Anabio Technologies Limited, Dublin (IE)

( * ) Notice: Subject to any disclaimer, the term of this patent is extended or adjusted under 35 U.S.C. 154(b) by 49 days.

(21) Appl. No.: 14/897,901

(22) PCT Filed: Jun. 11, 2014

(86) PCT No.: PCT/EP2014/062154
§ 371 (c)(1),
(2) Date: Dec. 11, 2015

(87) PCT Pub. No.: WO2014/198787
PCT Pub. Date: Dec. 18, 2014

(65) Prior Publication Data
US 2016/0120817 A1    May 5, 2016

(30) Foreign Application Priority Data

Jun. 12, 2013 (EP) .................................... 13171757

(51) Int. Cl.
| | |
|---|---|
| A61K 38/00 | (2006.01) |
| A61K 9/50 | (2006.01) |
| A61K 31/198 | (2006.01) |
| A61K 36/67 | (2006.01) |
| A23P 10/30 | (2016.01) |
| A23L 33/10 | (2016.01) |
| A23L 33/105 | (2016.01) |
| A23L 33/175 | (2016.01) |

(52) U.S. Cl.
CPC ............ *A61K 9/5052* (2013.01); *A23L 33/10* (2016.08); *A23L 33/105* (2016.08); *A23L 33/175* (2016.08); *A23P 10/30* (2016.08); *A61K 9/5089* (2013.01); *A61K 31/198* (2013.01); *A61K 36/67* (2013.01)

(58) Field of Classification Search
None
See application file for complete search history.

(56) References Cited

U.S. PATENT DOCUMENTS

2003/0215506 A1    11/2003   Kuhrts

FOREIGN PATENT DOCUMENTS

| WO | WO2007/069078 | 6/2007 |
| WO | WO2008/017962 | 2/2008 |

OTHER PUBLICATIONS

Serp D., et al "Characterization of an encapsulation device for the production of monodisperse alginate beads for cell immobilization," Biotechnol Bioeng. Oct. 5, 2000;70(1):41-53. Only two (2) pages of the Abstract.*
Moiety Definition Merriam-Webster 2018, 9 pages.*
Bowen, "Particle Size Distribution Measurement from Millimeters to Nanometers and from Rods to Platelets" Journal of Dispersion Science and Technology, 239(5):631-662, 2002.
Augustin et al., "Milk Protein-Based Microencapsulated Bioactives for Improving the Nutritive Value of Food," IDF World Dairy Summit, Capetown, South Africa, Nov. 4-8, 38 pages, 2012.
Gunasekaran et al., "Use of Whey Proteins for Encapsulation and Controlled Delivery Applications," Journal of Food Engineering 83(1):31-40, 2007.
Oliver and Augustin, "Using Dairy Ingredients for Encapsulation," Chapter 22, entitled "Using Daily Ingredients for Encapsulation," pp. 565-588 In Dairy-Derived Ingredients: Food and Nutraceutical Uses, 2009.

* cited by examiner

*Primary Examiner* — Jeanette M Lieb
(74) *Attorney, Agent, or Firm* — Occhiuti & Rohlicek LLP

(57) ABSTRACT

A process for producing microencapsulates comprising an active component such as creatine encapsulated within a polymerized hydrolyzed whey protein matrix is described. The method comprises the steps of providing a suspension of hydrolyzed whey protein and an active component in a carboxylic ester, treating the suspension to generate droplets of the suspension, and immediately curing the droplets by immersion in a basic curing solution, wherein the ester in the suspension reacts with the basic curing solution to release a salt that polymerizes the hydrolyzed whey protein encapsulating the active component in the presence of black pepper extract, glycerol, phosphate and optionally, astaxanthin and alpha lipoic acid.

10 Claims, 12 Drawing Sheets

E

F

A

B

| Size (μm) | Volume in % | Size (μm) | Volume in % | Size (μm) | Volume in % | Size (μm) | Volume in % | Size (μm) | Volume in % | Size (μm) | Volume in % |
|---|---|---|---|---|---|---|---|---|---|---|---|
| 0.020 | 0.00 | 0.142 | 0.01 | 1.002 | 2.43 | 7.096 | 2.28 | 50.238 | 0.00 | 355.656 | 0.00 |
| 0.022 | 0.00 | 0.159 | 0.02 | 1.125 | 2.97 | 7.962 | 1.70 | 56.368 | 0.00 | 399.052 | 0.00 |
| 0.025 | 0.00 | 0.178 | 0.03 | 1.262 | 3.57 | 8.934 | 1.24 | 63.246 | 0.00 | 447.744 | 0.00 |
| 0.028 | 0.00 | 0.200 | 0.05 | 1.416 | 4.20 | 10.024 | 0.88 | 70.963 | 0.00 | 502.377 | 0.00 |
| 0.032 | 0.00 | 0.224 | 0.08 | 1.589 | 4.84 | 11.247 | 0.60 | 79.621 | 0.00 | 563.677 | 0.00 |
| 0.036 | 0.00 | 0.252 | 0.10 | 1.783 | 5.43 | 12.619 | 0.42 | 89.337 | 0.00 | 632.456 | 0.00 |
| 0.040 | 0.00 | 0.283 | 0.13 | 2.000 | 5.97 | 14.159 | 0.19 | 100.237 | 0.00 | 709.627 | 0.00 |
| 0.045 | 0.00 | 0.317 | 0.18 | 2.244 | 6.38 | 15.887 | 0.00 | 112.468 | 0.00 | 796.214 | 0.00 |
| 0.050 | 0.00 | 0.356 | 0.25 | 2.518 | 6.65 | 17.825 | 0.00 | 126.191 | 0.00 | 893.367 | 0.00 |
| 0.056 | 0.00 | 0.399 | 0.33 | 2.825 | 6.73 | 20.000 | 0.00 | 141.589 | 0.00 | 1002.374 | 0.00 |
| 0.063 | 0.00 | 0.448 | 0.44 | 3.170 | 6.61 | 22.440 | 0.00 | 158.866 | 0.00 | 1124.683 | 0.00 |
| 0.071 | 0.00 | 0.502 | 0.57 | 3.557 | 6.29 | 25.179 | 0.00 | 178.250 | 0.00 | 1261.915 | 0.00 |
| 0.080 | 0.00 | 0.564 | 0.74 | 3.991 | 5.80 | 28.251 | 0.00 | 200.000 | 0.00 | 1415.892 | 0.00 |
| 0.089 | 0.00 | 0.632 | 0.95 | 4.477 | 5.16 | 31.698 | 0.00 | 224.404 | 0.00 | 1588.656 | 0.00 |
| 0.100 | 0.00 | 0.710 | 1.22 | 5.024 | 4.44 | 35.566 | 0.00 | 251.785 | 0.00 | 1782.502 | 0.00 |
| 0.112 | 0.00 | 0.796 | 1.55 | 5.637 | 3.68 | 39.905 | 0.00 | 282.508 | 0.00 | 2000.000 | 0.00 |
| 0.126 | 0.00 | 0.893 | 1.95 | 6.325 | 2.94 | 44.774 | 0.00 | 316.979 | 0.00 | | |
| 0.142 | | 1.002 | | 7.096 | | 50.238 | | 355.656 | | | |

C

— Raw Creatine Monohydrate (Form I)
— Spray-dried Creatine (Form II)
— Whey Protein (capsule material)
— Creatine encapsulated in *Hydrolysed* Whey Protein
— Creatine encapsulated in Hydrolysed Whey Protein + BioPerine
— Creatine encapsulated in *Native* Whey Protein
— Creatine encapsulated in denatured Whey protein

PROCESS FOR PRODUCING MICROCAPSULES COMPRISING AN ACTIVE COMPONENT ENCAPSULATED, PROTECTED AND STABILISED WITHIN A PROTEIN SHELL

CROSS-REFERENCE TO RELATED APPLICATIONS

This application is a U.S. national phase application filed under 35 USC § 371 of International Application No. PCT/EP2014/062154, which was filed Jun. 11, 2014, and which claims the benefit of the filing date of EP Application No. 13171757.1, which was filed Jun. 12, 2013. The entire content of these earlier filed applications is hereby incorporated by reference herein.

TECHNICAL FIELD

The invention relates to a process for producing microcapsules comprising an active component (core material) encapsulated within a protein matrix (shell). The invention also relates to micro-capsules comprising an active component encapsulated within a protein shell, and comestible products, especially sports nutritional products, comprising micro-capsules of the invention.

BACKGROUND TO THE INVENTION

Creatine is recognised as a dietary supplement capable of increasing muscle mass and muscle performance. It is provided in a number of different forms, but the main form is a creatine monohydrate, provided as a powder.

The ergogenic effect of Creatine has been a subject of systematic investigation since the late 1970's. To date, more than 300 sport-related studies have been performed, some 80% of these studies demonstrated significant positive effects of creatine on muscle mass, muscle power, lean body mass and performance at maximum, short duration muscle exertion in various types of sports. Today, creatine monohydrate is the most significant nutrition supplement in the field of sports.

A popular form of Creatine Monohydrate is CREAPURE™ marketed by AlzChem as a power supplement. The instructions that accompany the product recommend that the powder is added to a warm drink at a dose of 1 g per 100 mls. This means that in order to ingest the recommended dose of 3 g per day, a user will have to ingest 300 mls (at least) of a warm drink. In addition, the literature for the product indicates that the powder has no long term stability in water, which means that the product must be made up shortly before it is ingested (<10 minutes) and cannot be stored during the day.

In addition to creatine itself, namely creatine monohydrate, numerous creatine salts such as creatine ascorbate, citrate, pyruvate and others have in the meantime likewise proved to be suitable nutritional supplements. European patent EP 894 083 and German published patent application DE 197 07 694 A1 may be mentioned as representative prior art at this point.

Uptake of creatine from the intestine and transport into the muscles is controlled by an NaCl-dependent creatine transporter and may be promoted by the simultaneous intake of carbohydrates and proteins. It has therefore been found that in comparison with sole intake of creatine, the combination of creatine and carbohydrates can lead to a 60% greater rise in creatine content in the muscle (Green A. L., Hultman E., Macdonald I. A., Sewell D. A., Greenhaff P. L. Carbohydrate ingestion augments skeletal muscle creatine accumulation in during creatine supplementation in humans. Am J. Physiol. 1996 November; 271 (5 Pt 1): E821-6). Further formulations have been suggested to improve creatine uptake into the body. Patent application DE 10 2006 050 931.5 accordingly describes a solid or aqueous alkaline preparation comprising a creatine component, which contains a buffer system which establishes a pH value of 8.0-12.0.

US 2003215506 claims a formulation which enhances the creatine transport, said formulation containing IGF-1 modulating substance, in particular proteins, colostrum and recombinant IGF-1. Apart from its undisputed ergongenic and physiological effects, Creatine Monohydrate suffers from a number of limitations, including low solubility/hydration capacity and poor stability in aqueous solutions, and the fact that relatively large doses are required to elicit an ergogenic effect in the body. Since creatine does not have marked stability in water or corresponding aqueous solutions, creatine cyclising by elimination of water will generate creatinine. The rate of cyclisation is dependant on the pH value of the solution and the temperature. Intestinal concentration does not play any role in this process. Conversion to creatinine proceeds rapidly in particular in the acidic pH range between 3 and 4. The rapid break-down of creatinine in this medium virtually rules out the use of aqueous or moist formulations for human and animal nutrition. For example, based on the stomach pH alone, a significant breakdown of creatine to creatinine can occur depending on the residence time. (Greenhaff, P. L.: Factors Modifying Creatine Accumulation in Human Skeletal Muscle. In: Creatine. From Basic Science to Clinical Application. Medical Science Symposia Series Volume 14, 2000, 75-82).

The stated disadvantages of the prior art with regard to creatine solubility and stability in aqueous solution and subsequent uptake from the intestine and transport into the target tissue, give rise to the object of the present invention of providing encapsulated preparations of creatine, which better protect creatine than previously demonstrated. In this way, breakdown of creatine to creatinine can be avoided and lead to improved creatine uptake from the intestine. Hence, it is an object of the invention to overcome at least one of the above-referenced problems.

One vital factor, however, is the optimum uptake and thus retention of the creatine in the target tissue. A further object of the invention was to ensure that the creatine absorbed from the intestine is optimally taken up into the target tissue and is not excreted as such via the kidneys or converted into creatinine, which is useless to the body and must likewise be excreted from the body via the kidneys. Therefore the encapsulated systems have acceptable organoleptic properties with improved bioavailability for food and beverage applications.

The majority of creatine in the human body is in two forms, either the phosphorylated form making up 60% of the stores or in the free form which makes up 40% of the stores. The average 70 kg young male has a creatine pool of around 120-140 g which varies between individuals depending on the skeletal muscle fiber type and quantity of muscle mass. The endogenous production and dietary intake matches the rate of creatinine production from the degradation of phosphocreatine and creatine at 2.6% and 1.1%/d respectively. In general, oral creatine supplementation leads to an increase of creatine levels within the body. Creatine can be cleared from the blood by saturation into various organs and cells or by renal filtration.

Three amino acids (glycine, arginine and methionine) and three enzymes (L-arginine: glycine amidinotransferase, guanidinoacetate methyltransferase and methionine adenosyltransferase) are required for creatine synthesis. The impact creatine synthesis has on glycine metabolism in adults is low, however the demand is more appreciable on the metabolism of arginine and methionine.

Creatine ingested through supplementation is transported into the cells exclusively by CreaT1. However, there is another creatine transporter Crea T2, which is primarily active and present in the testes. Creatine uptake is regulated by various mechanisms, namely phosphorylation and glycosylation as well as extracellular and intracellular levels of creatine. Crea T1 has shown to be highly sensitive to the extracellular and intracellular levels being specifically activated when total creatine content inside the cell decreases. It has also been observed that in addition to cytosolic creatine, the existence of a mitochondrial isoform of Crea T1 allows creatine to be transported into the mitochondria. Indicating another intra-mitochondrial pool of creatine, which seems to play an essential role in the phosphate-transport system from the mitochondria to the cytosol. Myopathy patients have demonstrated reduced levels of total creatine and phosphocreatine as well as lower levels of CreaT1 protein, which is thought to be a major contributor to these decreased levels.

It is an object of the invention to overcome at least one of the above-referenced problems.

STATEMENTS OF INVENTION

In a first aspect, the invention relates to process for producing microcapsules comprising an active component encapsulated within a polymerised hydrolysed protein matrix, the method comprising the steps of providing a suspension of hydrolysed protein and an active component in a liquid ester, treating the suspension to generate droplets of the suspension, and immediately curing the droplets by immersion in a basic curing solution, wherein the ester in the suspension reacts with the basic curing solution to release a salt that polymerises the hydrolysed protein encapsulating the active component. The Applicant has surprisingly found that microcapsules formed according to the process of the invention are highly stable upon prolonged storage in aqueous solution. For example, after 28 days storage, creatine monohydrate encapsulated in hydrolysed whey protein showed almost no loss in creatine concentration (FIG. 9). Furthermore, creatinine (a breakdown product of creatine) was not detected at any significant levels after 28 days storage under the same conditions. Hence, it has been possible to show that the encapsulation system is capable of achieving the primary objective of the invention, namely stability in aqueous solutions.

In this specification, the term "active component" should be understood to mean an agent that is suitable for delivery to the gastrointestinal tract of a mammal, and includes pharmaceutically active agents, and health food supplements including vitamins, minerals, co-factors, amino acids and the like. Preferably, the active component is an active agent that partially and/or fully degrades in water/aqueous solution and is typically at least partially insoluble in water. Examples of such active agents include creatine moieties (for example creatine and its esters), beta-alanine, and amino acids, especially L-amino acids such as L-Leucine, L-glutamine and the Branched-Chain Amino Acids (BCAA's) typically comprising of Leucine, Isoleucine, and Valine. The active agent in the invention can comprise of one/more amino acids, which the body metabolizes in the stomach and intestines. The active agent can comprise one or more of the following amino acids such as isoleucine, alanine, leucine, phenylalanine, threonine, tryptophan, glycine, valine, proline, histidine, serine, tyrosine, glutamate, glutamic acid, and glutamine, in any form for example as salts, esters, branched-chain amino acid structures (BCAA's), complexes, precursors or derivatives.

The active component preferably comprises a creatine moiety, for example creatine, or a creatine precursor or derivative, examples of which include creatine monohydrate, guanidinoacetic acid (a direct precursor of creatine), creatine esters, creatinol. Creatinol O-phosphate, or a mixture of at least two of these compounds. Other creatine precursors include guanidinoacetic acid, creatine esters, creatinol and creatinol O-phosphate which are know to be converted into creatine in the body and in this manner are suitable encapsulation candidates for this specific delivery action. Creatine monohydrate and guanidinoacetic acid should be regarded as particularly preferred creatine moieties for the purpose of the invention.

The active component preferably is selected from a creatine moiety, L-Glutamine, Beta alanine, L-Leucine or a BCAA's amino acid, or derivatives or pre-cursors thereof. These amino acids are consumed by a large number of athletes and those interested in sports nutrition for a variety of reasons such as muscle mass gain, muscle recovery and increased energy. The vast majority of Glutamine, Leucine and Beta-Alanine in nutritional products is in the L conformation. Industry experts recommend consumption of glutamine as a powder or capsule due to instability in water and losses of the amino acids during digestion processes.

Leucine, along with isoleucine and valine is one of the branched-chain amino acids (BCAAs), which play an important role in sports nutrition. Leucine is an essential amino acid and as such cannot be synthesized in the body and must be derived from the diet. Hence, Leucine stability and bioavailability are vital. Generally speaking BCAA's make up 15% of a consumed protein. Even in high protein diets, levels of BCAA's including Leucine consumed may be low with a subsequent compromise on bioavailability during gastric transit. The ingredient is stable under ambient conditions; however the effect of gastric transit on free-form Leucine results in poor absorption in the mammalian system.

Glutamine is an amino acid and is not recognised as essential due to the body's ability to synthesize it. As the most abundant amino acid in the body, it constitutes a little more than five percent of the amino acids found in animal-derived protein sources such as meats, dairy, and eggs. The amino acid is consumed by a large number of athletes and those interested in sports nutrition for a variety of reasons such as muscle mass gain, muscle recovery and increased energy. Industry experts recommend consumption of glutamine as a powder or capsule due to stability issues with the glutamine in water. For this reason it is recommended to avoid products such as pre-made drinks and bars containing the free amino acid. Regardless of the form, up to 90 percent of ingested glutamine is eliminated during digestion due to lack of protection against digestive conditions. A fraction of consumed glutamine will survive beyond the liver due the action of digestive enterocytes and immune cells within the gut.

Beta-alanine is a nutritional supplement widely used by athletes and bodybuilders to improve performance. This nonessential amino acid occurs naturally in the body and is also found in foods such as chicken, beef, pork and fish.

Beta-alanine is the rate-limiting precursor of carnosine (EFSA), which potentially generates intramuscular carnosine and improved muscular endurance. Beta-alanine can be generally provided as either a powder or in gelatine capsules and its presence in foodstuffs can be measured by established methods (EFSAS). General dosage is 1.6-6.4 g of Beta-alanine per day for 4 weeks. However, an issue for Beta-alanine is parenthesis (pins and needles feeling) when administered in a large dose. An encapsulation delayed release strategy could benefit the consumer and manufacturers by alleviating this issue. Indeed, one manufacturer recommends consuming 3.2 g per day but breaking this amount into 2-3 doses per day. A delayed release formulation would add convenience to this product. At present there appears to be no example of microencapsulation of the product in literature.

For this reason these amino acids and Branched-chain structures (BCAA's) are suitable candidates for this formulation and delivery using the methods and products of the invention. When the aforementioned sources are added to ready-to-consume supplements it is usually in a peptide bound form such as glycyl-L-glutamine hydrate. Hence the amount of active component is ultimately limited and restricted per serving. Regardless of the form, on average, up to 92 percent of ingested active agents are eliminated during digestion. A fraction of consumed active agents will survive beyond the her due the action of digestive enterocytes and immune cells within the gut. In this manner, glutamine, Beta-alanine, L-leucine and BCAA's structure should be regarded as particularly preferred amino acid sources for the purpose of this invention.

Suitably, the suspension comprises an extract of *Piper nigrum* L (black pepper) or *Piper longum* L (long pepper), and which extract comprises 95% piperine (hereafter "pepper extract") wherein polymerisation of the hydrolysed whey protein encapsulates the active component and the pepper extract. Ideally, the extract is BioPerine (see www.bioperine.com).

The Applicant has discovered that incorporation of the pepper extract into the microcapsules enhances the absorption efficiency of the active component within the gastrointestinal tract (See FIG. 11), especially when the active component is a creatine moiety such as creatine monohydrate. The encapsulation system protects creatine better from conversion to creatinine in the stomach than previously. It was surprisingly found that the presence pepper extract in the encapsulation matrix lead to a distinctly better uptake from the intestine and exhibited distinctly higher bioavailability and are thus better taken up into the target tissue. Without being bound by theory, the Applicant believes that the electrostatic interaction between the active component and the pepper extract has the effect of increasing the electrostatic potential of the active component resulting in increased aqueous solubility and lipid solubility. This encapsulation system clearly provided favourable organoleptic properties. Suitably, in this structural format, creatine is encapsulated and stabilized by whey protein and Black Pepper Extract is further incorporated into the encapsulation matrix to aid creatine bioavailability in the blood. In the preferred embodiment of the invention, the combination of creatine monohydrate whey protein and phosphate and Black Pepper extract further enhance creatine encapsulation efficiency (>99.5%) with enhanced creatine bioaccessibility for the muscle contraction and exercise.

Preferably, the encapsulation system (i.e. the suspension) has a pH value of 3-6, ideally 3.5-4.8. The preferred initial carrier system is a mixture of an alcohol, acetic acid and hydrolysed protein (dairy protein origin is preferred). The amount of ester produced may be freely selected over a wide pH range, said preferred ratio being set at the selected pH value of the formulation which is established at pH 3-6, preferably above pH 4, ideally at 4.8. The advantage of that, if the mixture ratio is correctly selected, (alcohol:acid:protein), there is virtually no restriction on the amount of salt that can be released from the ester reaction for further encapsulation purposes. For instance, when a 1:1 mixture is used pH value greater than 4 is inevitably established, this being independent of the total amount of alcohol introduced. In this way, a pH value acceptable from an organoleptic aspect may be established and at the same tie the creatine is surprisingly well protected from the influence of acids, in particular gastric acid, so avoiding the conversion of creatine to creatinine. The excellent action of the encapsulation process of the invention could not be predicted in the claimed pH range.

It was surprisingly found that the use of the encapsulation process of the invention not only led to the reduced breakdown of creatine in the stomach, but that uptake for the administered creatine in to the cells is also improved. It has accordingly been possible to demonstrate that the present invention lead to a distinctly greater rise in creatine concentrations in the target tissue than is the case with un-encapsulated creatine monohydrate. In this connection, the use of sodium acetate salt in connection with the pepper extract (i.e. BioPerine) surprisingly demonstrated a significant influence on the bioavailability and uptake of creatine into cells. The encapsulation of creatine in the presence of pepper extract and sodium acetate salts for improving the uptake of creatine into cells has not hitherto been describe and offer distinct advantages over the previous practice of using elevated carbohydrate or protein doses.

Using the encapsulation process of the invention typically provides stability of creatine against acids and thus reduces the breakdown of creatine in the stomach. Moreover, the presence of pepper extract suitably improves the uptake of creatine into the cells and sodium ions of the acetate buffer further assist this process.

Typically, the active component is a creatine moiety. This means a molecule or complex comprising creatine, for example a creatine complex such as creatine monohydrate, or a creatine derivative or precursor such as guanidinoacetic acid (a direct precursor of creatine), creatine esters, creatine salts, creatinol. Creatinol O-phosphate, or mixtures of at least two of these compounds. Examples of creatine salts include creatine hydrochloride and creatine nitrate. However, the process of the invention is also applicable to the encapsulation of other active components, especially active components for oral delivery, for example glutamine, oil soluble bioactives such as vitamins and minerals, fatty acids, or fat soluble colours or flavours.

Suitably, the process includes an initial step in which the ester is formed in-situ, typically by reaction between an alcohol, preferably a weak alcohol, and an organic acid, preferably a weak organic acid, in the presence of the hydrolysed protein and/or the active component.

In one embodiment, the suspension comprises a phosphate moiety suitable for crosslinking hydrolysed protein in the formed microcapsules—this embodiment is particularly suitable when the active agent is a creatine moiety. The phosphate moiety may be, for example, a phosphate salt, such as disodium phosphate. This structural addition of phosphate cross-linkers into the extrusion matrix enhance immediate creatine absorption and metabolism and potentially enable the accelerated generation of high-energy molecules, ATP, during exercise and creatine loading. Suitably, the phosphate is added to the suspension at a concentration of 0.01M to 0.05M, typically about 0.01M to 0.03M, and ideally about 0.02M.

In a preferred embodiment of the invention, the suspension is formed by mixing the active component, acetic acid, a weak alcohol, and hydrolysed protein together to form a suspension of hydrolysed protein and active component in an acetate ester.

In a preferred embodiment of the invention, the suspension is formed by mixing a creatine moiety (i.e. creatine monohydrate), acetic acid, a weak alcohol, and hydrolysed protein together to form a suspension of hydrolysed protein and creatine moiety in an acetate ester.

The term "hydrolysed" means that the protein has been treated with protease enzymes to at least partially digest native protein. Suitably, the hydrolysed protein has a degree of hydrolysis (% DH) of 18-85%. Degree of hydrolysis (DH) is defined as the proportion of cleaved peptide bonds in a protein hydrolysate, and is determined using the OPA spectrophotometric assay, which involve the using N-acetyl-L-Cysteine (NAC) as the thiol reagent.

Preferably, the hydrolysed protein is hydrolysed whey protein, ideally hydrolysed whey protein obtained from milk, especially bovine milk. However, other types of hydrolysed protein may be employed including, for example, bovine collagen, pea, rice or non-whey milk proteins. A hydrolysed protein of choice would be from a dairy source ingredient with 90-95% protein (w/w) protein content. The ideal ratio for milk proteins β-lactoglobulin and α-lactalbumin would be 3:1 to 5:1, preferably approx. 4:1, more specifically, 85:15. Flavourzyme represents an ideal enzyme for hydrolysis of diary proteins for this presented invention. Flavourzyme is a protease-peptidase complex produced by submerge fermentation of a selected strain of *Aspergillu oryzae*, as produced by Novo Nordisk A/S. Ideally, utilise Flavoruzyme standardised in terms of Leucine Amino Peptidase Units (LAPS) by the manufacturer. Hydrolysates for the present invention are prepared using a measure amount of Flavourzyme with 1000 LAPU with defined hydrolysis conditions. Temperatures can be within the range of 35-65° C., preferably, 40-60° C., ideally 45-50° C. pH values can be within the range 4-9, preferably, 5-8, ideally 6.5-7.5. Hydrolysis is performed with an enzyme/substrate ratio (E/S) of 1/200, preferably, 1/150, ideally 1/100, on the basis of total protein content.

The step of treating the suspension to generate droplets may be carried out using conventional techniques, including use of extrusion optionally in combination with a break-up technique such as liquid jet break up. Such method may be carried out using an encapsulator (such as the InoTech encapsulator described in WO2010/119041). However, the droplets may be generated by means of other techniques including spray drying (http://www.niro.com) spray chilling (Microencapsulation for improved delivery of bioactive compounds in to foods, Champagne, C. P., Fustier, P., *Current Opinion in Biotechnology I Vol.* 18 (2), April 2007, 184-190), prilling (http://www.niroinc.com/food_chemical/prilling_encapsulation.asp) or coacervation (http://www.coacervation.com), the details of which will be known to those skilled in the art. All of these techniques generate droplets of suspension in a stable format (i.e. little or no polymerisation of hydrolysed protein) that are immediately immersed in the basic curing bath.

Typically, the suspension comprises hydrolysed (whey) protein, a phosphate moiety, and pepper extract in a liquid ester base.

Suitably, the basic curing solution for formation of microcapsules contains glycerol, preferably in an amount of 0.01 to 0.10M, and ideally in an amount of 0.04 to 0.07M. This has been found to reduce surface tension during droplet/capsule formation. The presence of glycerol in the basic curing solution will result in glycerol being contained in the microcapsule membrane, typically in an amount of about 0.05% glycerol, providing microcapsules capsules with satisfactory spherical shape and size (20-150 microns). Suitably, the presence of glycerol reduces surface tension during capsule formation and further contributes to enhanced creatine encapsulation efficiency (approx. 14.5% enhanced creatine yield). Furthermore, glycerol incorporation into creatine micro-capsules, has the potential to further enhance water holding capacity and fluid retention in the muscle during creatine absorption phase. In the preferred embodiment of the invention, the presence of glycerol within the encapsulation matrix potentially provides muscle with enhanced hydration and regeneration capacities. This presented invention highlights the need to include glycerol within the encapsulation matrix, in the presence of whey protein to ensure optimum encapsulation efficiencies and to further aid muscle fluid retention during and after creatine absorption.

Thus, in another aspect, the invention relates to process for producing microcapsules comprising an active component encapsulated within a polymerised hydrolysed protein matrix, the method comprising the steps of providing a suspension of hydrolysed protein and an active component in a liquid ester, treating the suspension to generate droplets of the suspension, and immediately curing the droplets by immersion in a basic curing solution, wherein the ester in the suspension reacts with the basic curing solution to release a salt that polymerises the hydrolysed protein encapsulating the active component, and wherein the basic curing solution comprises glycerol, suitable in an amount of 0.04%-0.07% (v/v).

In one embodiment, the step of generating droplets is configured to generate droplets having a core and a coating, in which the core comprises the suspension and the coating comprises hydroylsed protein in a liquid ester. One method of generating such droplets comprises using an extruder having dual, concentric, nozzles, in which the inner nozzle extrudes a core-forming stream and the outer nozzle extrudes the coating-forming stream. In this embodiment, the active agent is contained within the core, and the hydrolysed protein in the coating is polymerized when the droplets are immersed in the basic curing solution. This embodiment is suitable for generating microcapsules in which the suspension comprises a non-aqueous base/matrix, for example an oil-in-water emulsion. An example of such a base is one in which comprises a lipid soluble component. In such examples, the suspension additionally comprises the fat soluble component and a suitable dispersing agent, such as a fatty acid.

In one embodiment, the suspension comprises Astaxanthin (CAS Number 472-61-7). Typically, the addition of this scientifically proven antioxidant, Astaxanthin (CAS Number 472-61-7), into the suspension further enhances capsule longevity, shelf-life possibly enhance muscle total creatine content as compared to the ingestion of creatine monohydrate alone. Suitably, the presence of astaxantin in whey protein encapsulation matrices, will provide an additional protective barrier against water, to help further protect and retard creatine degradation into creatinine.

In the presence of an astaxanthinin hydrolysed protein formulation/suspension, a dispersing agent (i.e. fatty acid)

must be added to assist the dissolution of Astaxanthin with hydrolyzed protein. The dispersing agent is preferably an oil-based agent, for example a fatty acid, for example lipoic acid or palmitic acid. The addition of astaxanthin, in an oil-based agent such as lipoic acid or palmitic acid will optimize the homogenous dispersion of Astaxanthin throughout the encapsulation matrix. Suitably, the addition of Astaxanthin using an oil-based agent such as lipoic acid, to the encapsulation formulation, will potentially maximize creatine uptake by the human skeletal muscle when creatine monohydrate is ingested in an encapsulated form, as outlined above.

Thus, in one embodiment, the suspension comprises hydrolysed protein (ideally hydrolysed whey protein), an active agent, pepper extract, and astaxanthin dissolved in a dispersing agent.

In another embodiment, the suspension comprises hydrolysed protein (ideally hydrolysed whey protein), an active agent, pepper extract, a phosphate moiety, and astaxanthin dissolved in a dispersing agent.

The preferred embodiment of the invention has the potential to significantly improve creatine protection against stomach acid, (due to the presence of whey protein matrices); augment creatine absorption (due to the presence of black pepper extract and Astaxanthinin oil-based dispersions); enhance creatine uptake and retention in the muscle (assisted by the presence of glycerol), for enhanced ergogenic performance, bioavailability and bioaccessibility (possibly catalyzed by the presence of phosphate). Thus, in a preferred embodiment, the invention provides a method for producing microencapsulates comprising an active component (preferably a creatine moiety) encapsulated within a polymerised hydrolysed protein shell (preferably a polymerised hydrolysed whey protein shell), the method comprising the steps of:

mixing an organic acid, an alcohol, hydrolysed protein, and an active component to generate a suspension of hydrolysed whey protein and the active component in a liquid ester carrier;

treating the suspension to generate an aqueous formulation with addition of a phosphate moiety, a pepper extract, or both;

and treating the aqueous formulation to generate droplets and immediately immersing the droplets in a basic curing solution;

wherein the ester reacts with the basic curing solution to release a salt that polymerises the hydrolysed whey protein encapsulating the active component in the presence of the pepper extract, the phosphate moiety, or both.

In another preferred embodiment, the invention provides a method for producing microcapsules comprising an active component (preferably a creatine moiety) encapsulated within a polymerised hydrolysed protein shell (preferably a polymerised hydrolysed whey protein shell), the method comprising the steps of:

mixing an organic acid, an alcohol, hydrolysed protein, and an active component to generate a suspension of hydrolysed whey protein and the active component in a liquid ester carrier;

treating the hydrolysed protein suspension to generate an emulsion, with addition of astaxanthin, and optionally one or more of a phosphate moiety, and pepper extract, and emulsified in the presence of a dispersing agent;

treating the emulsion to generate droplets and immediately immersing the droplets in a basic curing solution optionally containing additional phosphate and glycerol;

wherein the ester reacts with the basic curing solution to release a salt that polymerises the hydrolysed protein encapsulating the active component in the presence of astaxanthin and lipoic acid, and optionally pepper extract, a phosphate moiety or both.

In the above embodiment, the droplets that are generated preferably comprise core and coating. This can be achieved using a dual, concentric, nozzle arrangement, in which the emulsion is extruded through an inner nozzle and a coating formulation, preferably comprising hydrolysed protein in a liquid ester, and optionally a phosphate moiety, is extruded through the outer nozzle. The coating formulation may also comprise the emulsion. The coating formulation must comprise hydrolysed protein in a liquid ester, but preferably does not comprise the active agent.

Preferably, the process has an encapsulation efficiency of 92-98% as determined using the following equation: Encapsulation efficiency (%)=((Total Loading Creatine−Creatine Losses)/Total Loading Creatine)×100

Suitably, the process employs creatine monohydrate, typically crystalline creatine monohydrate. Ideally, the crystalline creatine monohydrate has a prismoidal topography (see FIG. 2A). Typically, the creatine monohydrate is spray dried creatine monohydrate, ideally crystalline creatine monohydrate obtained by spray drying (typically at low temperature) an aqueous suspension of creatine monohydrate, ideally a suspension of creatine monohydrate in alcohol.

Microcapsules formed according to the above-mentioned embodiments of the invention were preferably prepared using the co-extrusion laminar jet break-up technique (Encapsulator 1, Inotech, Switzerland). The device is fitted with an inner nozzle (ranging from 20-300 µm) and an outer nozzle (ranging from 300-500 µm. Suitably, the liquid ester suspension is treated with phosphate and pepper extract (FORMULATION 1) and supplied to the inner nozzle via sterile filtration coupled to a peristaltic pump to assist the formation of liquid-core capsules. Alternatively, the liquid ester suspension is emulsified with pepper extract and Astaxanthinin and an oil-based agent such as alpha lipoic acid (FORMULATION II). Formulation I or II will flow through the inner nozzle and create the capsule inner core. The outer capsule membrane is formed using the creatine liquid ester in the presence of additional phosphate, supplied to the outer nozzle using an air pressure regulation enabling flow rates ranging from 5-10 Liters/hour, provided by a maximal 0.8 bar air pressure. Formulations (I or II) are extruded through a heated nozzle (20 µm-400 µm; 35° C.) into a weak basic environment. At this point, the pH increases and the ester reacts with the base to release an acetate salt that instantly polymerises the protein suspension with simultaneous encapsulation of BioPerine, glycerol, phosphate and bioactive material (creatine). If oil core capsules are produced, again, pH will increase releasing an acetate salt that instantly polymerises the protein suspension with simultaneous encapsulation of BioPerine, glycerol, phosphate, astaxanthin and alpha lipoic acid within the core with bioactive material (creatine). Having chosen flow rates that enable a stable jet of creatine droplets through the nozzles, frequency and electrostatic charge were set to have a stable bead chain visible in the strobe light and a circular dispersion of the drops during their fall into a gelling bath placed 15 cm under the nozzle. This gelling bath was 500 milliliter of di-sodium phosphate buffer in 10 mM MOPS with 0.04-0.07% w/v glycerol, pH 7.4 magnetically stirred, so that a vortex is visible. Droplet immersion of creatine into this inventive curing solution cause the instantaneous release of the acetate salt that polymerises the hydrolysed protein, which further encapsulates the creatine moiety within the capsule core and outer whey protein membrane.

As a result, FORMULATION I generates creatine monohydrate encapsulated in the presence of phosphate, glycerol and, black pepper, surrounded by an outer membrane of hydrolysed whey protein. FORMULATION II, generates creatine monohydrate encapsulated within an alpha-lipoic acid oil core in the presence of phosphate, glycerol and, black pepper, further surrounded by an outer membrane of hydrolysed whey protein. Creatine capsules are further incubated for 20 minutes in the basic curing buffer and washed twice with 10 mM MOPS, with a final wash performed with $H_2O$ DI for 30 minutes.

The term "microcapsule" as used herein should be understood to mean a particle comprising an active component encapsulated within a hydrolysed protein shell, and having an average diameter of less than 100 μm, 90 μm, 80 μm, 70 μm, 60 μm, 50 μm. Preferably, the microcapsule has an average diameter of less than 50 μm, 40 μm, 30 μm, or 20 μm. The method of measuring average diameter and D (v, 0.9) (size at which the cumulative volume reaches 90% of the total volume), of micro-capsules is determined using a laser diffractometer (Mastersizer 2000, Stable Micro Systems, Surrey, UK) with a range of 0.2-2000 μm. For particle size analysis, micro-bead batches were resuspended in Milli-Q water and size distribution was calculated based on the light intensity distribution data of scattered light.

The term "protein gel' as used herein should be understood to mean a sol in which the solid particles are meshed such that a rigid or semi-rigid mixture results. The rigidity of the gel structure will be determined by Texture Analyzer TA.XT Analyzer. A gel is placed under a probe and, by running a test, is compressed at 0.3 mm/sec until it collapses. The force (in grams) and the distance (in mm) are measured and give the mechanical strength of the gel. The process is made 4 to 6 times to ensure accuracy. The strength of one gel can be calculated by dividing the strength measured by the calculating the surface area of the gel particle under the probe.

Suitably, the suspension comprises 10-25% or 10-20% hydrolysed protein (w/v).

Typically, the suspension comprises 75-90% or 80-90% active component (w/v).

Optionally, the suspension further comprises:
0.01-0.05% pepper extract (w/v);
0.02-0.5 M phosphate moiety;
0.03-0.08% Astaxanthin (w/v); and
0.6-0.9% dispersing agent (w/v).

Thus, in one embodiment, the suspension comprises:
10-25% hydrolysed protein (w/v);
75-90% active component (w/v);
0.01-0.05% pepper extract (w/v);
0.02-0.5 M phosphate moiety;
0.03-0.08% Astaxanthin (w/v); and
0.6-0.9% dispersing agent (w/v).

In another embodiment, the suspension comprises:
10-20% hydrolysed protein (w/v);
80-90% active component (w/v);
0.01-0.05% pepper extract (w/v);
0.02-0.5 M phosphate moiety;
0.03-0.08% Astaxanthin (w/v); and
0.6-0.9% dispersing agent (w/v).

Preferably, the hydrolysed protein is hydrolysed whey protein. Preferably, the active agent is a creatine moiety. Preferably, the pepper extract is Bioperine. Preferably, the dispersing agent is a fatty acid. Preferably, the dispersing agent is alpha-lipoic acid.

In a particularly preferred embodiment, the suspension comprises:
10-20% hydrolysed whey protein (w/v);
80-90% creatine moiety (w/v);
0.025-0.035% BioPerine (w/v);
0.03-0.04 M phosphate moiety;
0.04-0.06% Astaxanthin (w/v); and
0.7-0.85% alpha-lipoic acid (w/v).

The term "liquid ester" should be understood to mean an ester of an organic acid in a liquid form. Suitably, the process includes an initial step in which the ester is formed in-situ, typically by reaction between an alcohol, preferably a weak alcohol, and an organic acid, preferably a weak organic acid, optionally in the presence of the hydrolysed protein and/or the active component.

The term "weak alcohol" should be understood to mean any of a large number of colorless, flammable organic compounds that contain the hydroxyl group (OH) and that slowly form esters with acids. Simple alcohols, such as methanol and ethanol, are water-soluble liquids, while more complex ones, like acetyl alcohol, are waxy solids. Names of alcohols usually end in -ol. Typical alcohol concentrations range from 0.2M-0.4 M (98% purity).

Examples of weak organic acids include lactic acid, acetic acid, formic acid, citric acid, and oxalic acid. Preferably, the acid is acetic acid. An organic acid is an organic compound with acidic properties. The most common organic acids are the carboxylic acids, whose acidity is associated with their carboxyl group —COOH. Sulfonic acids, containing the group —$SO_2OH$, are relatively stronger acids. Alcohols, with —OH, can act as acids but they are usually very weak. The relative stability of the conjugate base of the acid determines its acidity. Typically, the acid has a concentration of 0.5-0.65M.

Typically, the suspension has a concentration of carboxylic ester of 0.1-0.6M, preferably 0.2-0.4M, and ideally about 0.3M.

The invention also relates to a microcapsule formed according to the process of the invention.

The invention also relates to an article of commerce comprising a multiplicity of microcapsules formed according to the process of the invention.

The invention also relates to a comestible item, for example a food product or beverage for human consumption, comprising a multiplicity of microcapsules formed according to the process of the invention.

The invention also relates to a microcapsule comprising an active component encapsulated within a polymerised hydroylsed protein shall, the microcapsule having a diameter of less than 100 μm, 90 μm, 80 μm, 70 μm, 60 μm, 50 μm. Preferably, the microcapsules have an average diameter of less than 50 μm, 40 μm, 30 μm, or 20 μm.

Suitably, the microcapsule comprise pepper extract, ideally BioPerine, encapsulated within the polymerised hydrolysed protein shell.

Typically, the active component is a creatine moiety. This means a molecule or complex comprising creatine, for example a creatine complex such as creatine monohydrate, or a creatine derivative such as creatine ethyl ester or a creatine salt. Examples of creatine salts include creatine hydrochloride and creatine nitrate. However, the microcapsules of the invention may comprise alternative or additional, active components, especially active components for oral delivery, for example glutamine, oil soluble bioactives such as vitamins and minerals, fatty acids, or fat soluble colours or flavours. Suitably, the creatine monohydrate is crystalline creatine monohydrate. Ideally, the crystalline creatine monohydrate has a prismoidal topography (see FIG. 2A). Typically, the creatine monohydrate is spray dried creatine monohydrate, ideally crystalline creatine monohydrate obtained by spray drying (typically at low temperature) an aqueous suspension of creatine monohydrate, ideally a suspension of creatine monohydrate in alcohol.

Preferably, the microcapsule comprises a phosphate crosslinker, that crosslinks amino acids in the polymerised hydrolysed protein chains.

Preferably, the polymerised hydrolysed protein comprises glycerol.

Preferably, the hydrolysed protein is hydrolysed whey protein, ideally hydrolysed whey protein obtained from milk, especially bovine milk. However, other types of hydrolysed protein may be employed including, for example, bovine collagen, pea, rice or non-whey milk proteins for hydrolysing proteins. A hydrolysed protein of choice would be from a dairy source ingredient with 90-95% protein (w/w) protein content. The ideal ratio for milk proteins β-lactoglobulin and α-lactalbumin would be approx. 4:1, more specifically, 85:15. Flavourzyme represents an ideal enzyme for hydrolysis of diary proteins for this presented invention. Falvoruzyem is a protease-peptidase complex produced bu submerge fermentation of a selected strain of *Aspergillu oryzae*, as produced by Novo Nordisk A/S. Ideally, utilise Flavoruzyme standardised in terms of Leucine Amino Peptidase Units (LAPS) by the manufacturer. Hydrolysates for the present invention are prepared using a measure amount of Flavourzyme with 1000 LAPU with defined hydrolysis conditions. Temperatures can be within the range of 35-65° C., preferably, 40-60° C., ideally 45-50° C. pH values can be within the range 4-9, preferably, 5-8, ideally 6.5-7.5. Hydrolysis is typically performed with an enzyme/substrate ratio (E/S) of 1/200, preferably, 1/150, ideally 1/100, on the basis of total protein content.

Suitably, the microcapsules comprises 10-25% hydrolysed protein (w/v).

Typically, the microcapsule comprises 75-90% active component (w/v).

Optionally, the microcapsule comprises 1.0-0.5% pepper extract (w/v).

Preferably, the microcapsule comprises:
10-20% hydrolysed protein (w/v);
80-90% active component (w/v);
0.01-0.05% pepper extract (w/v);
optionally, a phosphate moiety;
Preferably, the microcapsule comprises:
10-20% hydrolysed protein (w/v);
80-90% active component (w/v);
0.01-0.05% BioPerine (w/v);
optionally, one or more of a phosphate moiety; 0.04-0.07% glycerol (w/v), 0.03-0.08% Astaxanthin (w/v), and 0.6-0.9% alpha-lipoic acid (w/v).

Preferably, the microcapsule comprises:
10-20% hydrolysed protein (w/v);
80-90% active component (w/v);
0.01-0.05% BioPerine (w/v);
a phosphate moiety;
0.04-0.07% glycerol (w/v);
0.03-0.08% Astaxanthin (w/v);
0.6-0.9% alpha-lipoic acid (w/v)

Microcapsules may be provided on the forms of powders, granular products, pastilles, capsules and tablets effervescent tablets, solutions and gel products have shown to be particular suitable administration forms. Depending on the particular specific application, it may be highly recommended to use the creatine preparation in combination with other active ingredient having a physiological effect.

Preferably, the microcapsules are stable in water for a period of at least 20 days, 25 days or preferably 28 days. In this specification, the term "stable" means that there is no loss of encapsulated active agent detectable after the time period for a 6.25% suspension of microcapsules in water (5 g microcapsules dry weight in 80 g water).

The encapsulation according to the invention also have potential benefits in animals, such that use in animals is also provided. If the described creatine formulations are used a feedstuff additive, administration should in particular be regarded as preferred for breeding and fattening animal and animals in competitive sport and in this connection, it is particularly preferable for horses, pigs and poultry and fish.

The invention also relates to an article of commerce comprising a multiplicity of microcapsules according to the invention. Preferably, the article of commerce is selected from a comestible product, suitably a comestible sports nutrition product, such as a food or beverage, or is provided in the form of a supplement, for example as a powder or a particulate material, or in the form of a unit dose product such as a tablet.

In a preferred embodiment, the invention relates to a beverage, typically a sports nutritional beverage, comprising a multiplicity of microencapsulates according to the invention suspended in a liquid carrier.

In another embodiment, the invention relates to a snack bar, typically a sports nutritional snack bar, comprising a multiplicity of microencapsulates according to the invention suspended in an edible carrier.

When the comestible product of the invention (for example beverage or snack bar) is a sports nutritional product, the gelled hydrolysed protein typically has a degree of hydrolysis of less than 50%, 40%, 30% or 20%. Otherwise, the gelled hydrolysed protein may have a degree of hydrolysis of 80-85%.

The Applicant has also discovered a method of preparing crystalline creatine monohydrate that provides crystals having a low particle size distribution (See FIG. 2B), an average particle size of less than 10 μm, and a stable crystalline structure. This is advantageous for applications where the crystalline creatine monohydrate is to be encapsulated. Thus, the invention also relates to crystalline creatine monohydrate having a substantially prismoidal topography. This is shown in FIG. 2A. Typically, at least 50%, 60%, 70%, or 80% (v/v) of the crystals have a particle size of 1 to 10 μm.

The invention also relates to a method of preparing crystalline creatine monohydrate having a narrow particle size distribution comprising the steps of preparing an aqueous suspension of creatine monohydrate, and spray drying the aqueous suspension to generate crystalline creatine monohydrate having a narrow particle size distribution. Typically, the spray drying step is carried out at a low temperature suitable range of 30-70 Degrees, preferable range 40-60, optimal range 50-55 degrees. The invention also relates to a crystalline creatine monohydrate formed according to a method of the invention.

The invention also relates to a non-therapeutic method of increasing athletic performance in an individual comprising the steps of administering to the individual a comestible product according to the invention in which the active component preferably comprises a creatine moiety, preferably creatine monohydrate, and wherein the microencapsulates in the preparation are typically broken down in the gastrointestinal tract of the individual to release the active component.

BRIEF DESCRIPTION OF THE FIGURES

The invention will be more clearly understood from the following description of some embodiments thereof, given by way of example only, with reference to the accompanying figures.

DETAILED DESCRIPTION OF THE INVENTION

Figure 1:
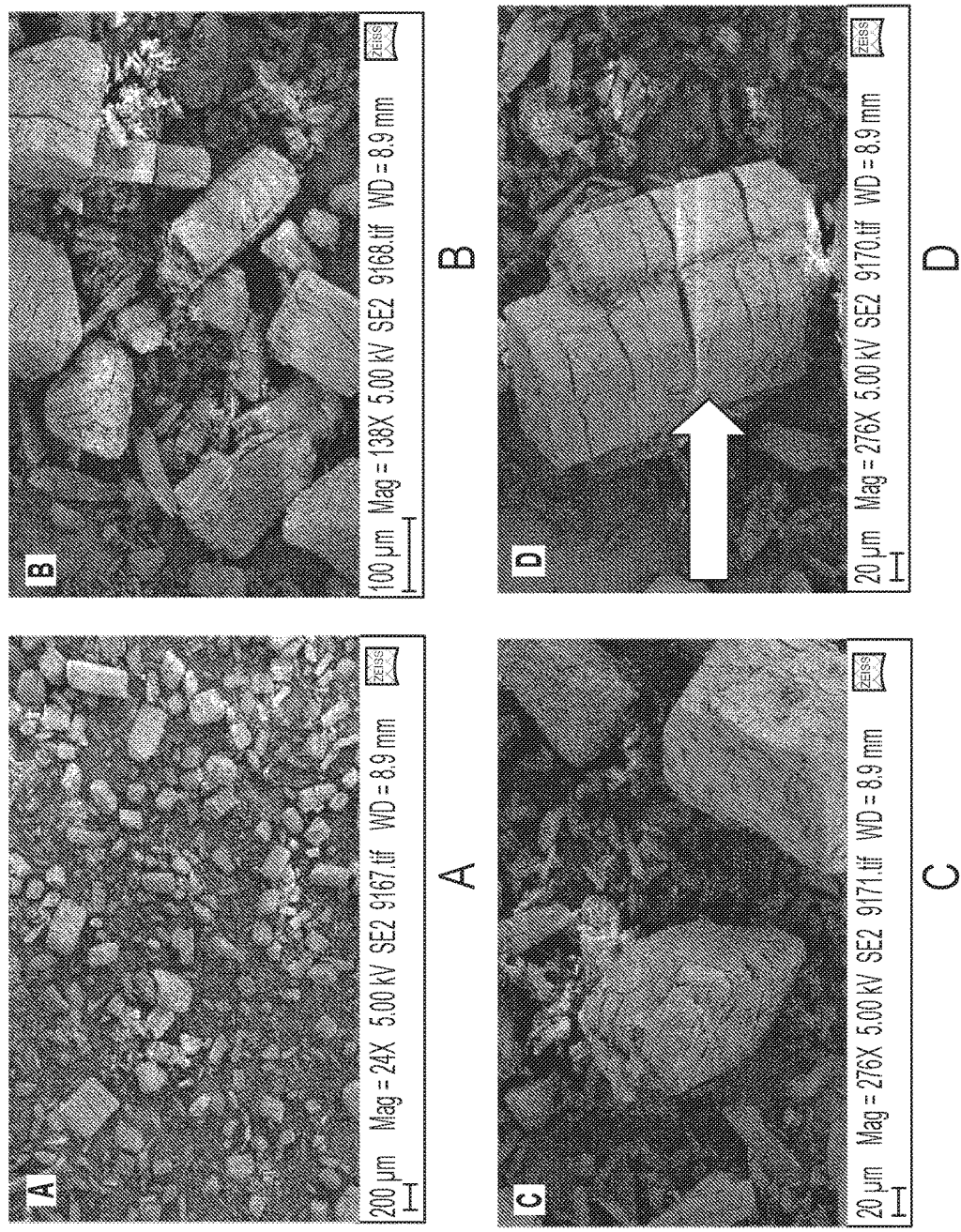
FIGS. 1. (A-D) is a scanning electron microscopy imagery of commercial creatine monohydrate as raw, and (E and F) illustrate size distribution of raw creatine.
Figure 1:
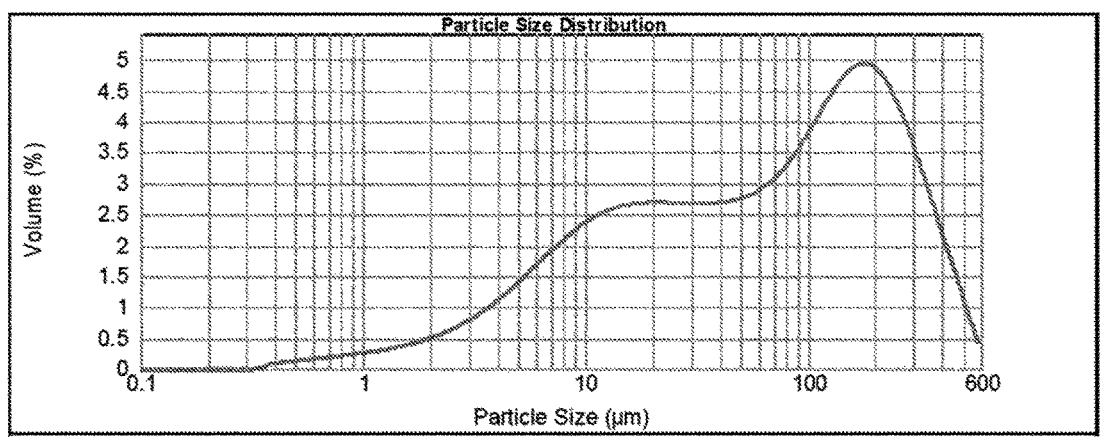

Broadly, the invention provides a method for a) controlling the timing of acetate-mediated polymerisation of milk proteins for the encapsulation of bioactive materials, with particular interest in Creatine monohydrate in the presence of black pepper extract and Astaxanthinand b) controlling the release of the encapsulated bioactive material by controlling phosphate cross-linking and digestion properties of the encapsulation system in order to enhance the absorption, uptake and muscle utility of active creatine. A technology has been developed that provides bioactive (i.e. Creatine monohydrate) with structural features for long term stability via encapsulation of an aqueous formulation that contains milk protein, Black Pepper extract, (BioPerine; CAS: 94-62-2), Astaxanthin (CAS AS 472-61-7) an alcohol, and an organic acid. This combination of substrates will naturally produce an ester, which subsequently produces a salt upon reaction with a weak base. This produces a polymerised protein matrix stabilised by intra-molecular disulphide bonds. Residual alcohol generated during this reaction is subsequently removed during the drying process. The incorporation of BioPerine to the formulation enhances creatine stability against stomach acid and enzymatic digestion on the lumal side of the gastrointestinal tract. As a result of the digestion characteristics of the hydrolysed whey protein capsules, encapsulated creatine will release at the proximal ileum, to enable absorption and uptake of creatine into the blood stream from the lumal side. In this way, absorption efficiency and bioavailability of creatine monohydrate is significantly enhanced as a result of encapsulation. Moreover, the additional presence of crosslinked phosphate will enable the accelerated generation of ATP during creatine administration, while the presence of glycerol will potentially enhance fluid retention during exercise and muscle contraction. The further incorporation of black pepper extract and/or astaxanthin in the presence of alpha lipoic acid further endorses the bioaccessibility of creatine for muscles. Furthermore, the presence of hydrolysed milk protein eliminates the allergenic nature of the final product. This method provides mild process conditions for the production of functional, bioavailable Creatine monohydrate for beverage applications. Previous inventions failed sufficiently protect Creatine monohydrate from heat and low pH during storage and delivery in beverage formats with added functional ingredients to enhance bioavailability in the blood and subsequent bioaccessibility in the muscle.

This novel process for stabilisation of bioactive material has the ability to combine, protect and release functional ingredients at site specific absorption sites in the gastointestinal tract to achieve synergistic ergogenic effects with enhanced hydration capacity to assist longterm muscle contraction. Creatine capsules are small (<50 microns), monodispersed, homogenous and spherically shaped stabilised particles, with a narrow size distribution, using a short production time, under mild and simple encapsulation conditions with low costs and high encapsulation efficiencies (% of product encapsulated) for commercial production with the additional bioavailable attributes.

A process for specialised encapsulation process has been developed for bioactive components and the presented invention utilises Creatine monohydrate as the test material. Aqueous suspensions are prepared for initial molecular crystalisation in the presence of crosslinking agents followed by extrusion encapsulation. The technology enables the production of aqueous core capsules or oil-core capsules thorough incorporation of astaxathin using an oil-based dispersing agent.

Step 1: Molecular Stabilisation

Scanning Electron Microscopy provided a valuable tool for the visualisation and ultimate optimization of the best encapsulation system for efficacy delivery of bioactive materials such as Creatine Monohydrate. Below is an image of free Creatine monohydrate (FIG. 1). It is clear that the structure of raw Creatine monohydrate is highly unstable as a monohydrate material.

Figure 2:
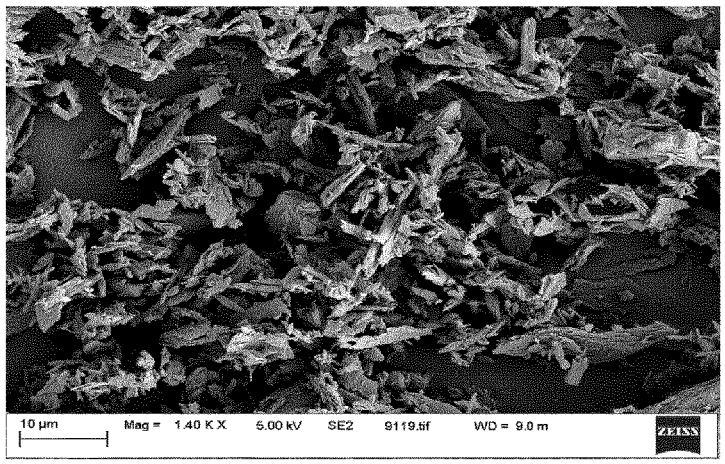
FIG. 2. Creatine monohydrate structure (A) and size distribution (B) and (C) of creatine after spray drying in the presence of pharmaceutical grade ethanol.
Figure 2:
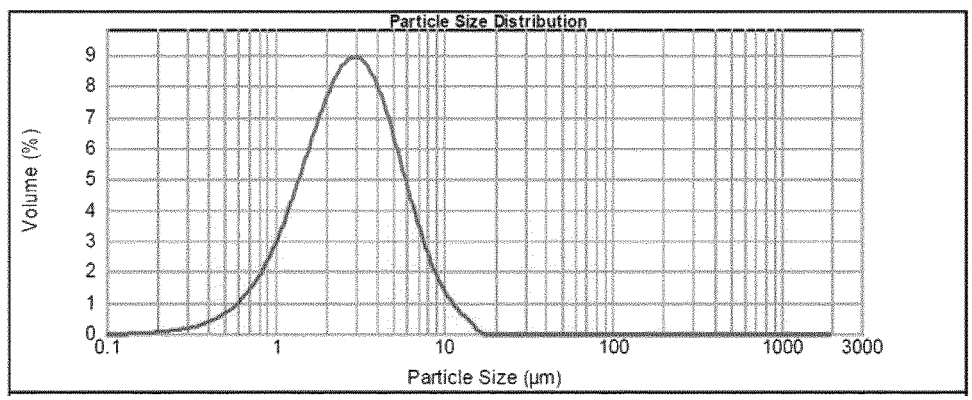

Large particles shown in FIGS. 1A-1D illustrate the potential to breakdown into smaller particles with a greater hydration capacity. FIG. 1D illustrates dehydration layers which typically correspond to an unstable compound (see arrows on FIG. 1). FIGS. 1E and F further illustrate the unfavourable broad size distribution of commercially available Creatine Monohydrate. The size of the particles rang from microns to over 600 microns. This is not acceptable for stability or further encapsulation applications. Hence, before initiating encapsulation procedures, it was imperative to generate a Creatine material with 1) an even size distribution and ii) a stable crystalline structure. In order to achieve this objective, Creatine monohydrate was spray-dried using pharmaceutical grade Ethanol at lower temperature, which maintained all functional attributed of Creatine. Following spray-drying, the Creatine material produced was assessed for suitable i) size distribution and ii) stability in a crystalline form. FIG. 2A illustrates a Creatine product with a prismodial topography which ultimately generates a crystalline material with a large surface area. This is a positive attribute since the magnitude of bonding with encapsulation polymer will be greater. Moreover, Malvern instrumentation further validated the use of this material for encapsulation due to the presence for suitable particle size less than 10 microns. This represents significant progress for the initial step toward optimization of the encapsulation process at a low cost. This initial drying procedure is 50% less than typical drying methodologies due to the low. Hence, we estimate this step to cost approx. €0.20-0.30 per kg produced.

Step 2: Encapsulation
Production of Aqueous Encapsulation Systems:

Micro-dispersed whey protein micro-capsules are prepared based on laminar jet break-up (Serp et al., 2000) for the generation of whey protein micro-capsules loaded with creatine monohydrate and BioPerine. In the present study, the liquid ester carrier is delivered to the nozzle via a feed line, utilizing a single nozzle with diameter ranging from 20-1000 μm. The nozzle is connected via a PTFE membrane to a vibrating device, which was insulated from the surrounding structures by rubber mounts to avoid the generation of resonance frequencies in the system. Aqueous formulations are prepared comprising of the bioactive material (i.e. Creatine monohydrate), milk protein, a pharmacological agent (i.e. weak alcohol) and an organic acid (i.e. acetic acid). This combination of substrates naturally produces an acetate ester, stable at room temperature. However, no salt is present to initiate protein polymerisation; therefore the suspension remained in a fluid state. This creatine liquid ester is treated with phosphate and black pepper extract (FORMULATION 1) and fed to the nozzle via sterile filtration coupled to a peristaltic pump to assist the formation of aqueous capsules. The protein-creatine-ester blend is aseptically extruded through the assigned nozzle to generate a steady stream of droplets regulated by air pressure enabling flow rates ranging from 10-15 Liters/hour, provided by a maximal 0.6-0.8 bar air pressure.

Having chosen flow rates to generate a stable jet of droplets through the nozzles, frequency and electrostatic charge were set to have a stable bead chain visible in the strobe light and a circular dispersion of the drops during their fall into a gelling bath, an alkaline phosphate buffer (0.4M) placed 15 cm under the nozzle. The basic gelling bath with continuous agitation to avoid coalescence or flocculation of micro-capsules during curing.

A charge can also be applied to the mononuclear droplets to enable their dispersion and prevent coalescence occurring in the air and/or upon impact resulting in the formation of duplets and/or larger gelled particles. This charge must be applied at values ranging between 0.8-1.1 mV. Upon landing in the phosphate gelling bath, droplet movement can be retarded momentarily due to the high surface tension, which can again result in the formation of irregular shaped gelled particles. In some instances this delay can cause the droplet to burst, releasing the creatine liquid ester carrier before encapsulation takes place. Hence, surface tension can be reduced by the addition of a surfactant and/or by slightly heating (50-60° C.) the phosphate solution. This will enable quicker entry of the drop into the solution preventing its deformation and resulting in an immediate encapsulation and high efficiencies. For this reason, it is essential to include glycerol in the phosphate gelling bath with a tempered temperature of 35 degrees celcius. The presence of glycerol in the gelling bath will also result in glycerol incorporation into the final creatine capsule. Due to the fact that glycerol has favourable hydration properties for muscle function, the inclusion of glycerol in the encapsulation system has a functional and ergogenic benefit. The gelling bath was 500 milliliter of di-sodium phosphate buffer in 10 mM MOPS with 0.04-0.07% w/v glycerol, 0.6-0.9% (w/v) alpha lipoic acid, pH 7.4 magnetically stirred, so that a vortex is visible. Droplet immersion of creatine into this inventive curing solution cause the instantaneous release of the acetate salt that polymerises the hydrolysed protein, which further encapsulates the creatine moiety within the gelled structure in the presence of black pepper extract phosphate and glycerol.

During jet break-up and/or when entering the gelling bath, a high negative charge was induced onto their surface using an electrical potential of 0-2.15 kV between the nozzle and an electrode, placed directly underneath the nozzle. As creatine droplets fell through the electrode, they were deflected from their vertical position resulting in their impact occurring over a larger area in the gelation solution. This enabled mono-disperse capsules with a standard size deviation of less than ±1.5% to be generated.

Within the gelling bath, several instantaneous reactions occur. When the droplet enter the gelling bath, the pH increases and the ester reacts with the base to release an acetate salt that instantly polymerises the protein suspension with simultaneous encapsulation of BioPerine, glycerol, phosphate and bioactive material (creatine). This reaction produces residual amounts of alcohol, which is subsequently removed during the final drying process, which alleviates further food application issues.

Pliable micro-beads were cured/polymerized at room temperature in the phosphate buffer, recovered, washed twice in sterile water and matrix characterization was performed as a function of cure time in buffer (0-180 min) and washed twice with 10 mM MOPS, with a final wash performed with $H_2O$ DI for 30 minutes. Optimum parameters for a given protein-creatine suspension were logged and utilized without adjustment during further batch production. The production of <50 mL of micro-beads was sufficient to meet the requirements of preliminary studies; hence the encapsulator resembled a batch-reactor. Commercial production of aqueous gel creatine particles has been opitmised based on the aforementioned principle. As a result, this aqueous encapsulation methodology generates creatine monohydrate encapsulated in the presence of phosphate, glycerol and, black pepper, in a gelled hydrolysed whey protein matrix.

Preparation of Oil-Core Encapsulation Systems:

For the production of oil-core encapsulation systems, a concentric system with two running liquids is essential for the generation of micro-capsules with addition oil cores. This is achieved by simultaneously supplying two feed lines to a specifically designed concentric nozzle unit. In turn, this will generate a co-extruded laminar liquid jet, subsequently broken-up into mononuclear drops, by the application of a vibrational frequency. The creatine liquid ester carrier is then gelled into the desired mononuclear micro-capsules with respective inner oil core and whey protein outer membrane.

The capsule diameter is mainly dependent on the diameter of the outer nozzle and like the single nozzle system used for aqueous systems; the size can be varied within a certain range by increasing/decreasing the applied flow rate and vibrational frequency. The diameter of the internal nozzle and the flow rate of the material will also affect the final capsule size with increasing diameters and volumes resulting in larger core volumes, therefore, larger micro-capsules.

Micro-dispersed whey protein micro-capsules were prepared based on laminar jet break-up (Serp et al., 2000) for the generation of whey protein micro-capsules loaded with creatine monohydrate and BioPerine. In the present study, the liquid ester carrier was delivered to the nozzle via a feed line, utilizing two nozzles with diameters in the range 20-1000 µm. The nozzle was connected via a PTFE membrane to a vibrating device, which was insulated from the surrounding structures by rubber mounts to avoid the generation of resonance frequencies in the system. Oil-based formulations are prepared comprising of the bioactive material (i.e. Creatine monohydrate), milk protein, a pharmacological agent (i.e. weak alcohol) and an organic acid (i.e. acetic acid). This combination of substrates naturally produces an acetate ester, stable at room temperature. However, no salt is present to initiate protein polymerisation; therefore the suspension remained in a fluid state. This creatine liquid ester is emulsified with black pepper extract, Astaxanthin, and an oil-based agent such as alpha lipoic acid (FORMULATION II). This formulation will flow through the inner nozzle (heated at 35 degrees celcius) and create the capsule inner core. The outer capsule membrane is formed using the creatine liquid ester in the presence of additional phosphate, supplied to the outer nozzle using an air pressure regulation enabling flow rates ranging from 5-10 Liters/hour, provided by a maximal 0.7-0.9 bar air pressure.

At this point, the pH increases and the ester reacts with the base to release an acetate salt that instantly polymerises the protein suspension with simultaneous encapsulation of BioPerine, glycerol, phosphate, astaxanthin and alpha lipoic acid within the core with bioactive material (creatine). This reaction produces residual amounts of alcohol, which is subsequently removed during the final drying process, which alleviates further food application issues.

Having chosen flow rates that enable a stable jet of creatine droplets through the nozzles, frequency and electrostatic charge were set to have a stable bead chain visible in the strobe light and a circular dispersion of the drops during their fall into a gelling bath placed 15 cm under the nozzle. The production of <50 mL of micro-beads was sufficient to meet the requirements of preliminary studies; hence the encapsulator resembled a batch-reactor. The protein-creatine-ester blend is aseptically extruded through the assigned nozzle into tempered (35° C.) alkaline phosphate buffer (0.4M) with continuous agitation to avoid coalescence or flocculation of micro-capsules during curing. This gelling bath was 500 milliliter of di-sodium phosphate buffer in 10 mM MOPS with 0.04-0.07% w/v glycerol, pH 7.4 magnetically stirred, so that a vortex is visible. Droplet immersion of creatine into this inventive curing solution cause the instantaneous release of the acetate salt that polymerises the hydrolysed protein, which further encapsulates the creatine moiety within the capsule core and outer whey protein membrane.

A charge can also be applied to the mononuclear droplets to enable their dispersion and prevent coalescence occurring in the air and/or upon impact resulting in the formation of duplets and/or larger microcapsules. This charge must be applied at higher values compared to the monocentric nozzle system to enable similar droplet dispersion to be achieved. This is due to the smaller percentage of polyelectrolyte present in the droplet because of the core material. Upon landing in the phosphate gelling bath, droplet movement can be retarded momentarily due to the high surface tension, which can again result in the formation of oval shaped capsules. In some instances this delay can cause the droplet to burst, releasing the creatine liquid ester carrier before encapsulation takes place. It is hypothesized that this bursting is caused by the movement of the core liquid out through the pre-hardened membrane protein when capsules are been held back briefly at the surface of the hardening solution and hence results in release (bursting) of the core creatine liquid. Surface tension can be reduced by the addition of a surfactant and/or by slightly heating (50-60° C.) the phosphate solution. This will enable quicker entry of the drop into the solution preventing its deformation and resulting in an immediate encapsulation and high efficiencies. For this reason, it is essential to include glycerol in the phosphate gelling bath with a tempered temperature of 35 degrees celcius. The presence of glycerol in the gelling bath will also result in glycerol incorporation into the final creatine capsule. Due to the fact that glycerol has favourable hydration properties for muscle function, the inclusion of glycerol in the encapsulation system has a functional and ergogenic benefit.

During jet break-up and/or when entering the gelling bath, a high negative charge was induced onto their surface using an electrical potential of 0-2.15 kV between the nozzle and an electrode, placed directly underneath the nozzle. As creatine droplets fell through the electrode, they were deflected from their vertical position resulting in their impact occurring over a larger area in the gelation solution. This enabled mono-disperse microcapsules with a standard size deviation of less than ±1.5% to be generated. Within the gelling bath, several instantaneous reactions occur. When the droplet enter the gelling bath, the pH increases and the ester reacts with the base to release an acetate salt that instantly polymerises the protein suspension with simultaneous encapsulation of BioPerine, glycerol, phosphate and bioactive material (creatine). This reaction produces residual amounts of alcohol, which is subsequently removed during the final drying process, which alleviates further food application issues.

Pliable micro-beads were cured/polymerized at room temperature in the phosphate buffer, recovered, washed twice in sterile water and matrix characterization was performed as a function of cure time in buffer (0-180 min) and washed twice with 10 mM MOPS, with a final wash performed with $H_2O$ DI for 30 minutes. Optimum parameters for a given protein-creatine suspension were logged and utilized without adjustment during further batch production. The production of <50 mL of micro-beads was sufficient to meet the requirements of preliminary studies; hence the encapsulator resembled a batch-reactor. Commercial production of aqueous gel creatine particles has been opitmised based on the aforementioned principle. As a result, this aqueous encapsulation methodology generates creatine monohydrate encapsulated in the presence of phosphate, glycerol and, black pepper, in a gelled hydrolysed whey protein matrix. As a result, this oil-based encapsulation system generates creatine monohydrate encapsulated within an alpha-lipoc acid oil core in the presence of phosphate, glycerol and, black pepper, further surrounded by an outer membrane of hydrolysed whey protein.

The incorporation of BioPerine to the formulation enhances the absorption efficiency of the bioactive within the gastro-intestinal tract and the presence of hydrolysed milk protein eliminates the allergenic nature of the final product. This formulation has been optimised for the production of >1,000 kilos of encapsulated bioactive in a single batch production under sterile conditions.

The proposed aqueous and oil-core microcapsules containing encapsulated creatine can be manufactured using the aforementioned techniques on large-sale (>400 Liter per day) using vibrating jet technology and subsequently dried using conventional drying techniques (i.e. drum drying (http://www.gmfgouda.com) or fluidised bed drying (http://www.niroinc.com) for storage and subsequent addition to a beverage long drink or shot to assist creatine bioavailability in the blood and, more importantly bioaccessibility to the muscle during exercise (pre-, post- and loading phases).

X-ray diffraction (XRD) is a versatile, non-destructive technique utilised to detail the chemical composition and crystallographic structure of Creatine monohydrate before and after the encapsulation process. In order to better convey an understanding of the fundamental principles of X-ray diffraction instruments, the following terms are defined:

Amorphous: The atoms are arranged in a random way similar to the disorder we find in liquid water. Whey protein is amorphous.

Crystalline: A crystal lattice is a regular three-dimensional distribution (cubic, rhombic, etc.) of atoms in space. These are arranged so that they form a series of parallel planes separated from one another by a distance d, which varies according to the nature of the material. For any crystal, planes exist in a number of different orientations—each with its own specific d-spacing.

Commercial Creatine monohydrate (Raw) is in crystalline form I but it is desired to generate a more stable Crystal, known as crystalline form II. Based on the principle of X-ray diffraction, FIG. 3 reveals the progress of Creatine stability from chemical perspective. In the commercial form, Creatine exists in crystal form I, which is highly unstable and reactive to free water. After molecular stabilisation, Creatine monohydrate appear to be less amorphous i.e. less vulnerable to potential Creatinine production. XRD analysis also serves as a successful method to determine encapsulation efficiency of the system since Creatine is crystalline and whey protein (encapsulation matrix) is amorphous. Hence, if Creatine is successfully encapsulated by Whey Protein, XRD analysis will not show any crystalline structures i.e. all Creatine molecules are enveloped by amorphous whey protein. However, if Creatine is only partially encapsulated by Whey Protein, XRD analysis will reveal crystalline material i.e. some crystalline Creatine is still free and not interacting with Whey Protein.

Figure 3:
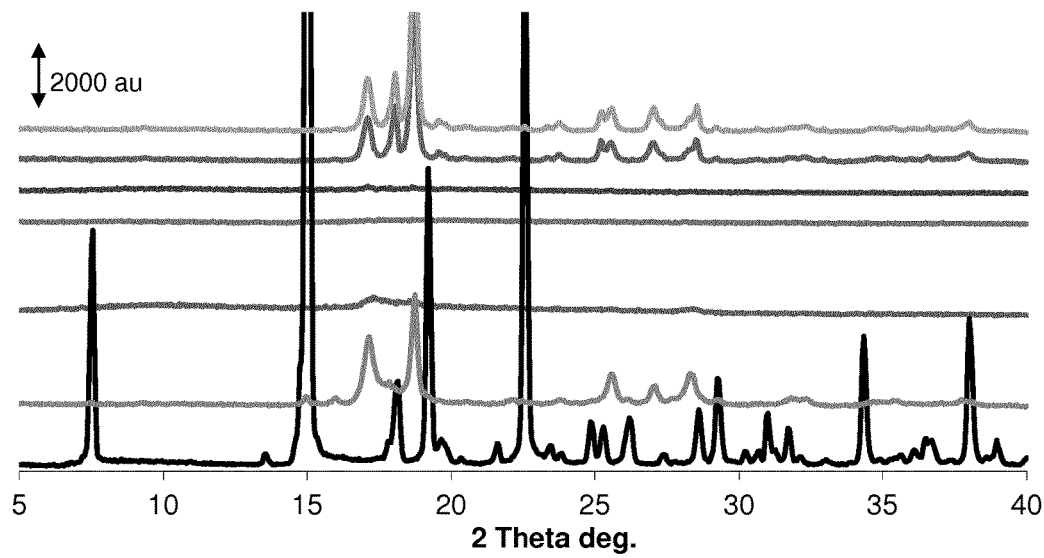
FIG. 3. X-ray diffraction data for consecutive steps within encapsulation process according to one embodiment of the invention.
Figure 4:
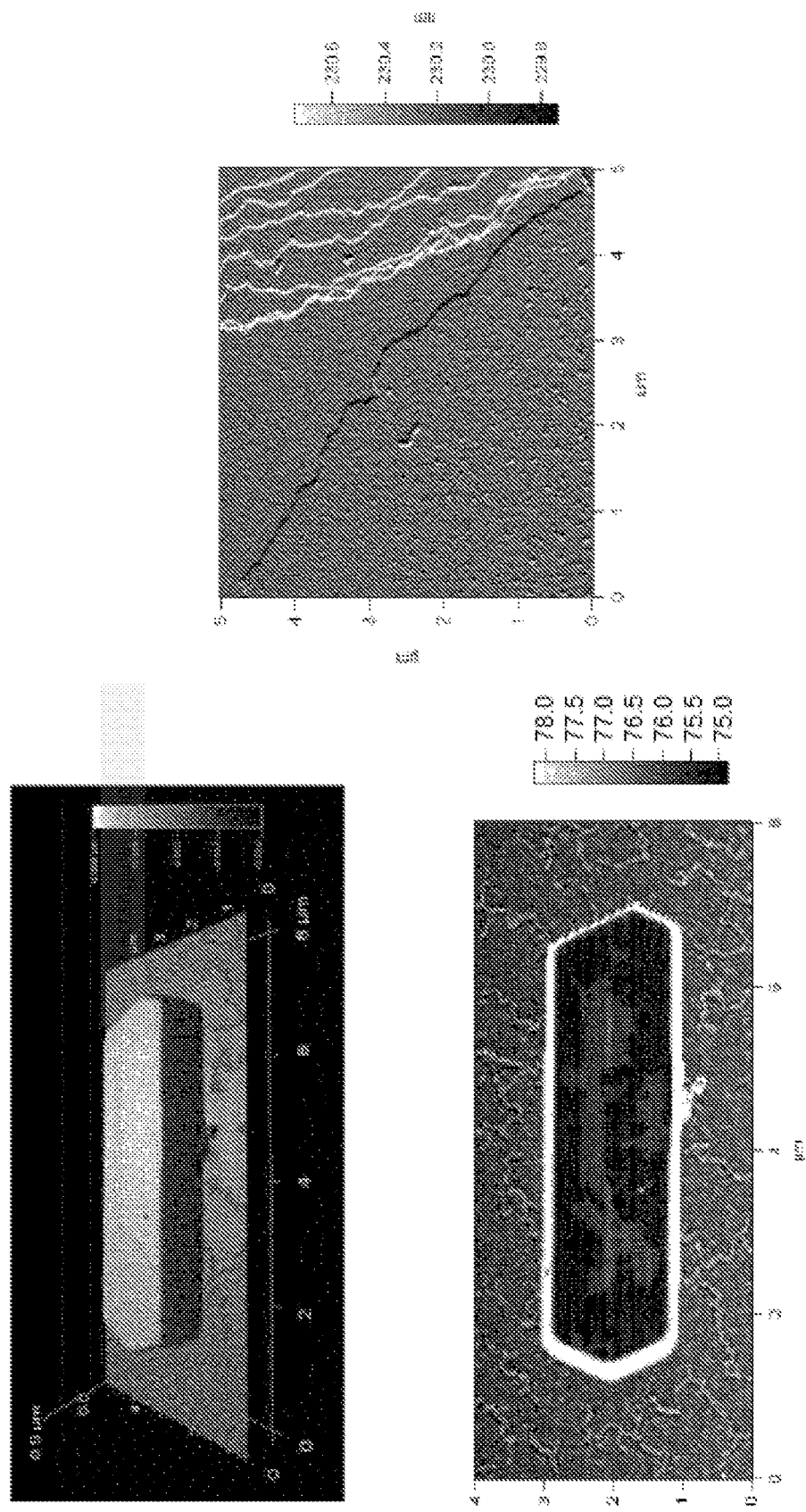
FIG. 4. Atomic Force Microscope (AFM) illustrates the presence of creatine crystal form II creatine within milk protein encapsulation matrices.

In FIG. 3, XRD data illustrate commercial (raw) Creatine monohydrate on the black baseline to be clearly crystalline due to the range of peaks presented at regular intervals in the graph. This is crystalline form I due to the intensity of two peaks mid-way along the profile. Following molecular stabilisation using low-temperature spray-drying, crystalline form II is generated. This is clearly evident due to the lesser intensity of crystalline peaks illustrated for the orange profile. Whey Protein encapsulation material was also analysed to confirm this amorphous form of Whey Protein and this was validated in the Green profile line. During the encapsulation process (step II), specialised hydrolysed whey protein demonstrated successful encapsulation efficiency for Creatine monohydrate. Interestingly addition of BioPerine did not adversely affect the encapsulation efficiency and full encapsulation capacity in the XRD profile (purple). However utility of native and denatured Whey Protein failed to successfully encapsulate Creatine. Based on these results, it is evident that Creatine is efficiently encapsulated using hydrolysed Whey Protein in the presence of BioPerine, for enhanced absorption capacity. It is clear that STEP 1 generated an appropriate molecular structure for efficient Creatine encapsulation with hydrolysed whey protein, in the presence of BioPerine.

Atomic Force Microscopy (AFM) illustrates embedded Creatine Monohydrate crystals within milk protein encapsulation systems. This is the ideal scenario for Creatine protection against water i.e. Crystal form II. Individual Creatine Crystals may solely occupy a whey protein capsule (approx. size, 10-20 micron); however the functionality remains the same per batch of encapsulated Creatine produced.

Thermal Stability

Figure 5:
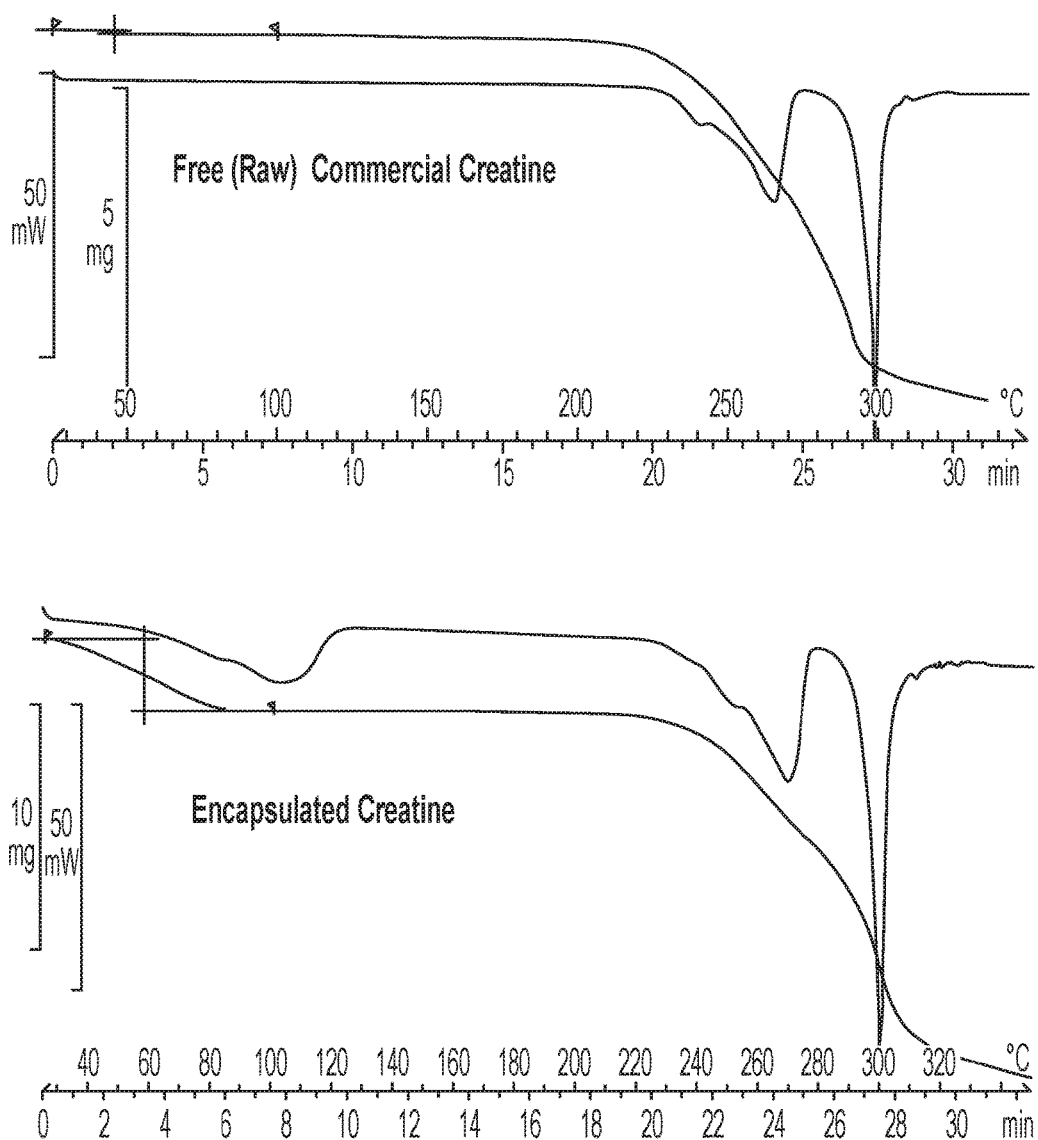
FIG. 5: Thermal gravimetrical analysis (TGA) of free creatine and encapsulated creatine.

Thermal Gravimetrical Analysis (TGA) in FIG. 5 illustrates no change in the thermal properties or compositional structure of commercial Creatine as a result of encapsulation. This analysis demonstrated that the degradation temperature of Creatine remained unchanged pre- and post-encapsulation. Hence, in the presence of encapsulation structures, Creatine does not exhibit undesirable degradation features. Furthermore, weight fluctuations were unaffected by changes in temperature, which illustrates that the Creatine monohydrate retained compositional structure and reactive properties following the encapsulation process.

Figure 6:
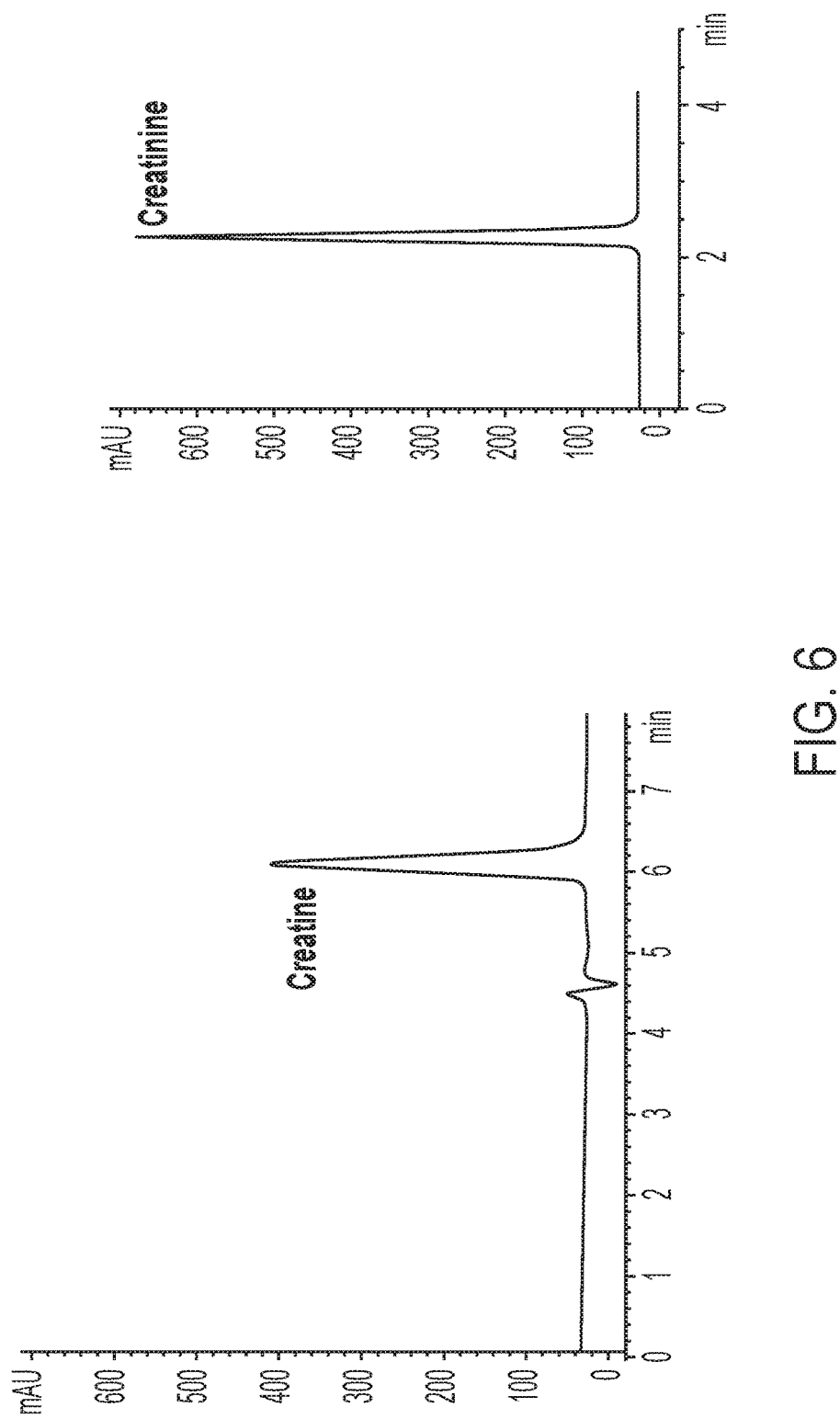
FIG. 6: Creatine and creatine detection by HPLC chromatography whereby creatine eluted after 2.25 minutes and creatine generated a narrow peak after 6.1 minutes.
Figure 7A:
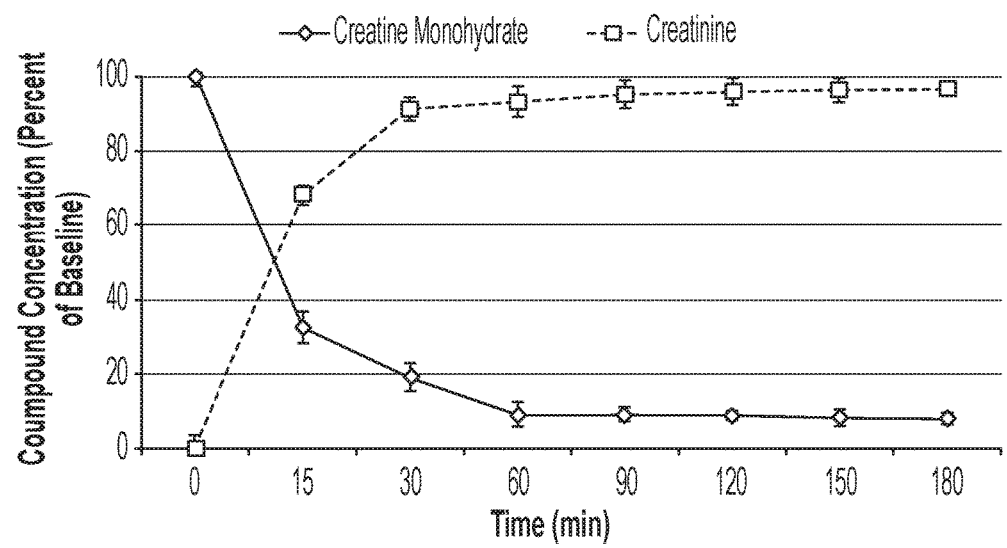
FIG. 7(A): Commercial Creatine monohydrate degradation in the aqueous incubation medium compared to encapsulated Creatine (B). Standard deviation is the average for 11 independent studies.
Figure 7B:
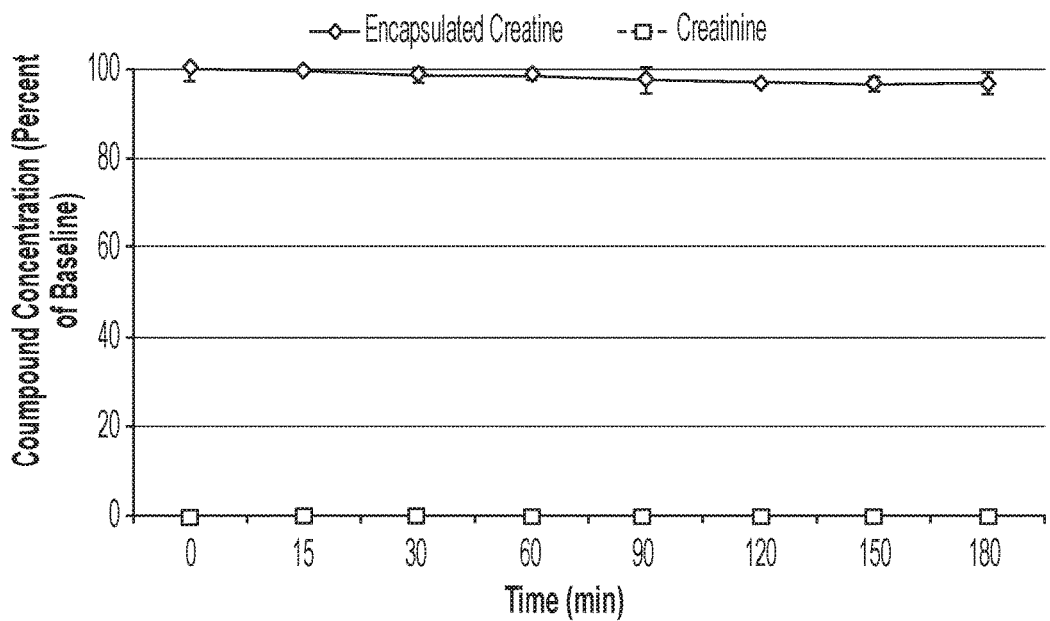

Creatine and Creatinine concentrations were detected (FIG. 6) using a standardised HPLC methodology. Following validation of the HPLC technique, stability trials were performed for free and encapsulated Creatine in water at 25° C. for 10 hours. Results demonstrated that degradation of free Creatine followed first-order kinetics. The first-order degradation rate constant was calculated as 0.0263 per day at 25° C. for free Creatine monohydrate, as derived from the slope of the line. Substantial conversion of Creatine into Creatinine was recognised in aqueous formulations, which demonstrated significant differences to that identified for encapsulated Creatine. Encapsulated formats revealed no Creatine conversion to Creatinine in the presence of water after 12 hours and continued storage for 48 hours also failed to identify any Creatinine production. This validates the encapsulation conditions utilised for the protection of Creatine for beverages applications, specifically for sports supplementation. FIG. 7 illustrates the creatine content reduction in water. Data clearly illustrates that commercial Creatine monohydrate concentration is reduced by 66% following 15 min incubation in water at room temperature. After 1 hour, 9%±1.34% of the initial Creatine concentration was still present. This reduction demonstrates a direct correlation with creatinine formation after 15 minutes increasing. In contrast, encapsulated creatine was significantly more stable in water solution after 3 hours at room temperature with no significant detection of Creatinine reported. Hence, encapsulation of Creatine represents potential delivery vehicle for Creatine monohydrate in aqueous beverage. Following this, accelerated shelf-life tests were conducted with final sports drink samples (formulated according to industrial standards) and encapsulated Creatine demonstrated >36 month shelf-life stability in aqueous environments. Furthermore, HPLC analysis confirmed the absence of Creatinine after completion of shelf-life testing. Hence, encapsulated Creatine fulfilled the stability Criteria for storage of beverage formulations.

The present invention comprises the development of milk protein encapsulation vehicles with desired mechanical rigidity (resistance to deformation) and strength (resistance to fracture) in order to structurally protect Creatine Monohydrate from aqueous (water) solutions during long storage times with concomitant release at the required systemic target site. Microencapsulates of the invention demonstrate acceptable long-term storage stability (36 months) with further sustained stability in simulated stomach conditions in the presence of pepsin. Microscopy and chromatography further validated the targeted disintegration of protein matrices in physiological intestinal conditions after several minutes with BioPerine providing enhanced absorption capacity. It should be noted that micro-bead degradation is catalysed by the synergistic effect of neutral pH and enzymatic action; a property which may be exploited for this specialised Creatine sports supplement application. For this reason, optimization of encapsulation conditions represented the basis of creatine stabilisation in the presence of Creatine protective chaperons i.e. milk protein and BioPerine. Due to the fact that bioperine is highly lipophilic, the concentration of bioperine will potentially increase the lipophilicity of the creatine compound and improve its ability to diffuse through biological membranes. Secondly creatine is a very lipophobic compound and needs a transporter to cross lipid-rich cells' plasma membranes. Research performed generated a stable Creatine-milk protein-BioPerine moiety that demonstrated a reduced degradation to creatinine and increased half-life in aqueous solutions. Hence, encapsulation in hydrolysed milk protein represents an excellent matrix for site-specific controlled delivery and release of Creatine with subsequent promotion of its absorption at their target site. Microscopy in FIG. 8 visualises the progress of Creatine encapsulation in real-time.

Figure 8A:
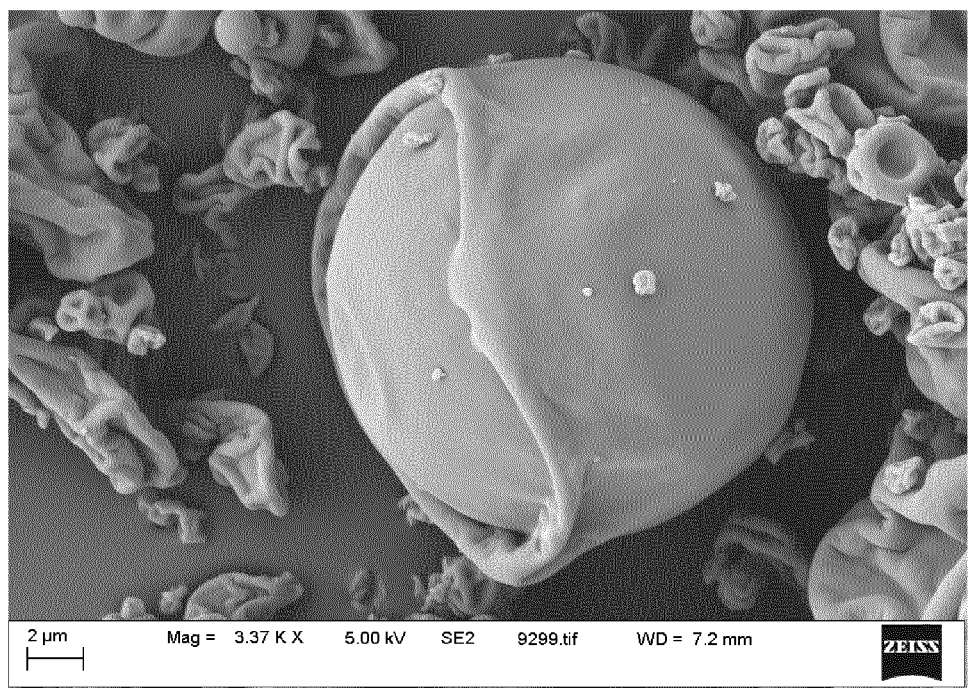
FIG. 8. Scanning Electron microscope image of (A) an incomplete coating of Creatine using native whey protein; (B) a single Creatine encapsulated particle and (C) additional hydrolysed protein coating (D) initial intestinal digestion of a micro-particles after exposure to intestinal contents with subsequent release of Creatine (E) for absorption into the bloodstream.
Figure 8B:
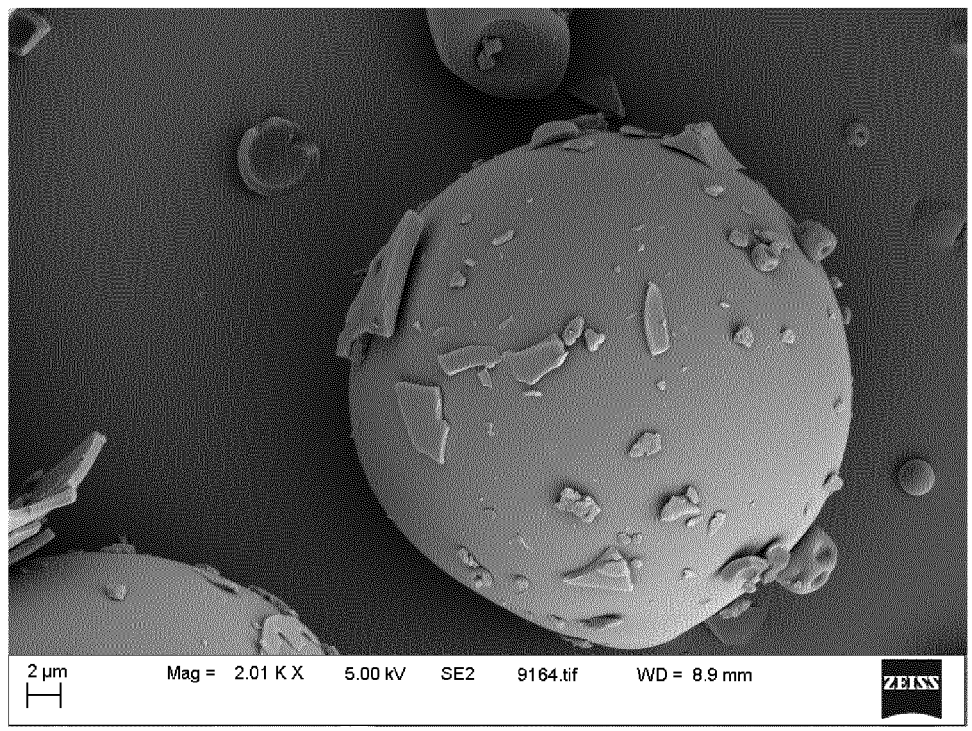
Figure 8C:
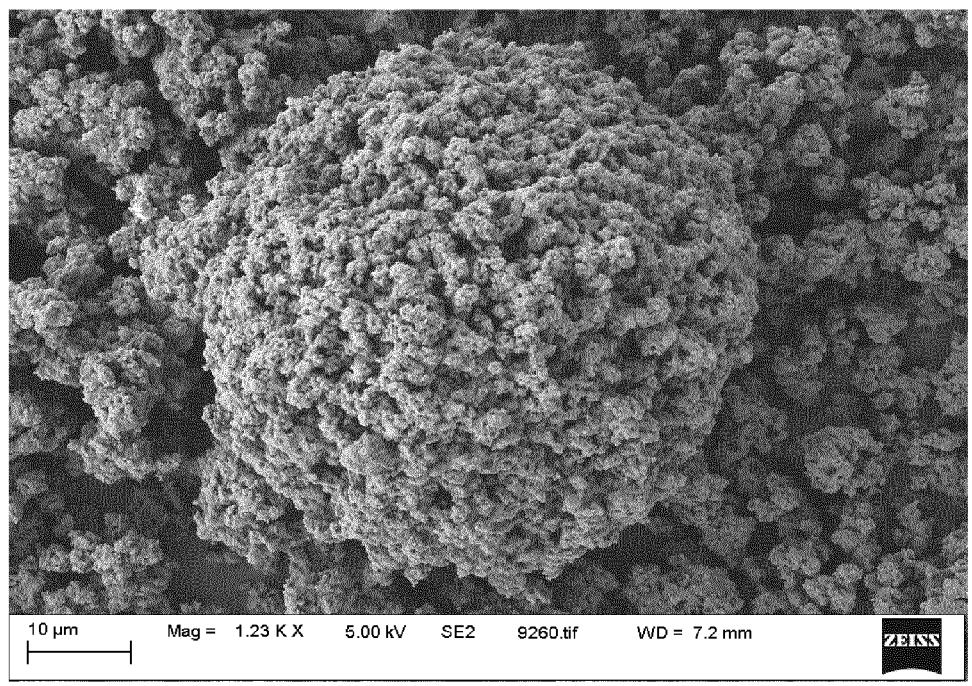
Figure 8D:
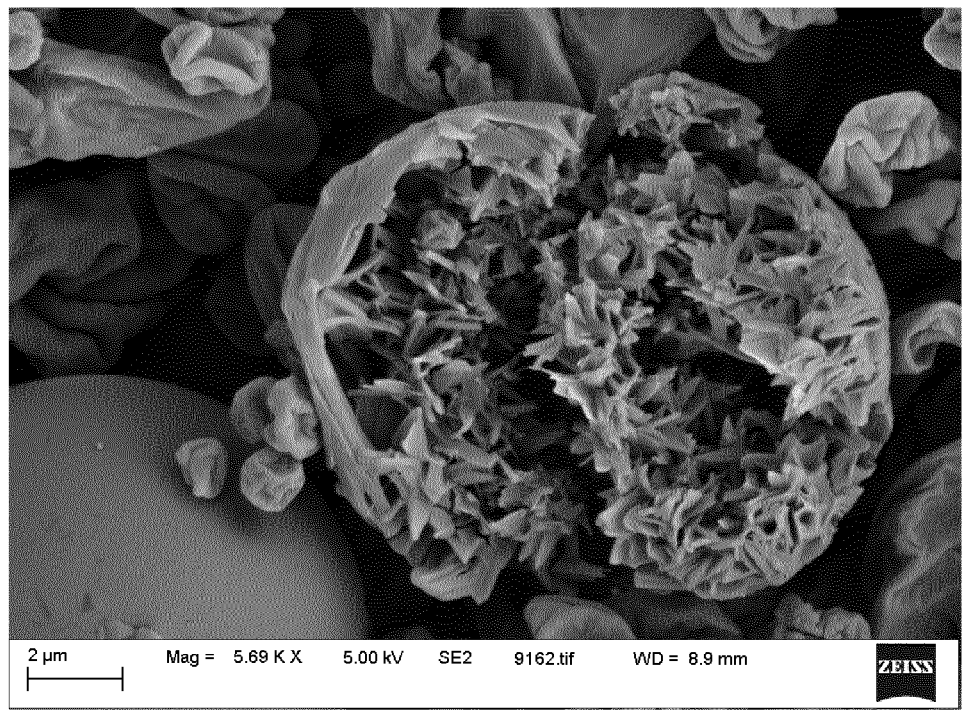
Figure 8E:
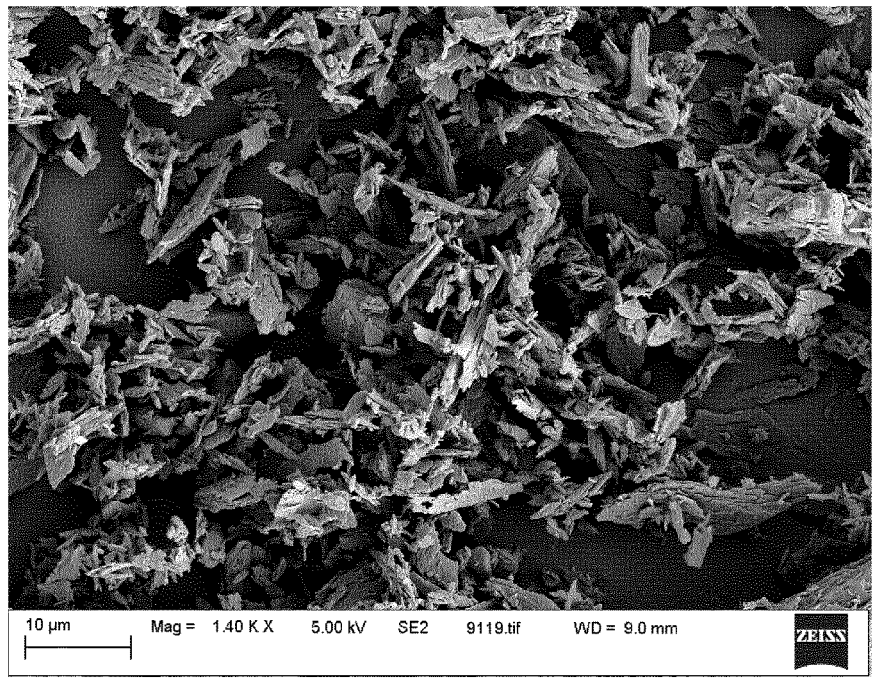

Microscope imagery illustrates the partial encapsulation of Creatine using native whey protein (A) according to the same process. This clearly exemplifies the short-fall of native protein compared to the efficient functional performance of hydrolysed protein as an encapsulation matrix (FIG. 8B). The encapsulation system was optimised to achieve the ideal encapsulation conditions for hydrolysed protein matrices as illustrated in FIG. 8C showing Creatine encapsulated in whey protein with BioPerine outer membrane layers. Following intestinal incubation, microcapsule digestion was clearly observed in FIG. 8D, which illustrates the erosion of protein matrix material as a result of the enzymatic action of intestinal contents. Following 3 minute intestinal incubation, Creatine monohydrate was fully released for subsequent absorption.

Creatine Storage Stability and Ex Vivo Digestion

Figure 9:
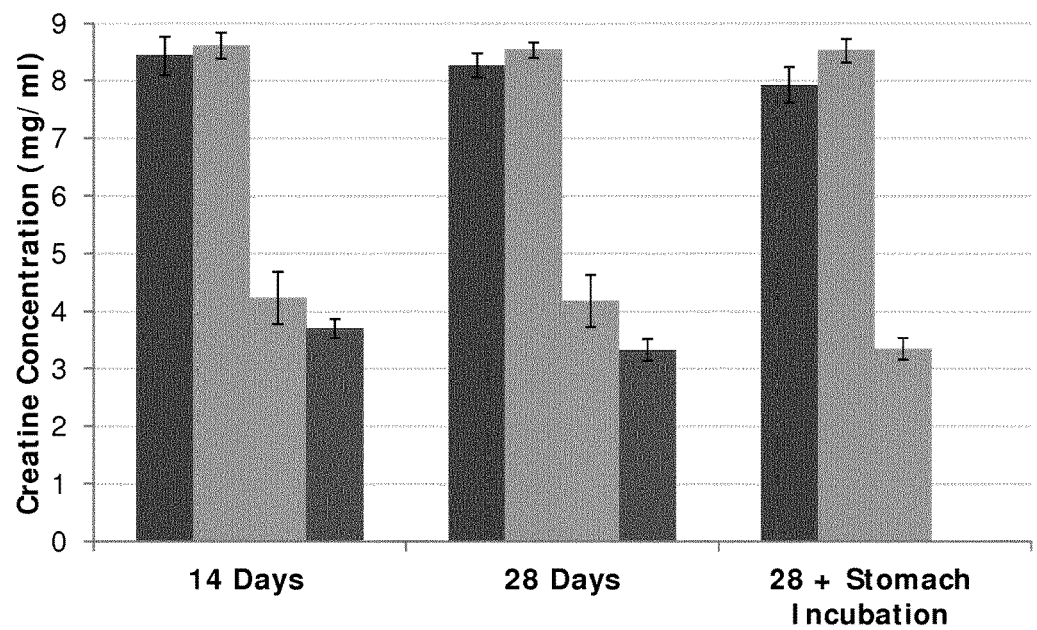
FIG. 9. Concentration of Creatine Monohydrate during 28-day storage in aqueous solution at pH 4.0 at room temperature. Treatments include hydrolysed milk protein capsules (■); hydrolysed milk protein capsules+BioPerine (■); native whey protein capsules (■) and Creatine in denatured whey protein capsules (■) at 25° C. for up to 28 days followed by exposure to ex vivo stomach contents (pH 1.6; 3 hours).
Figure 10:
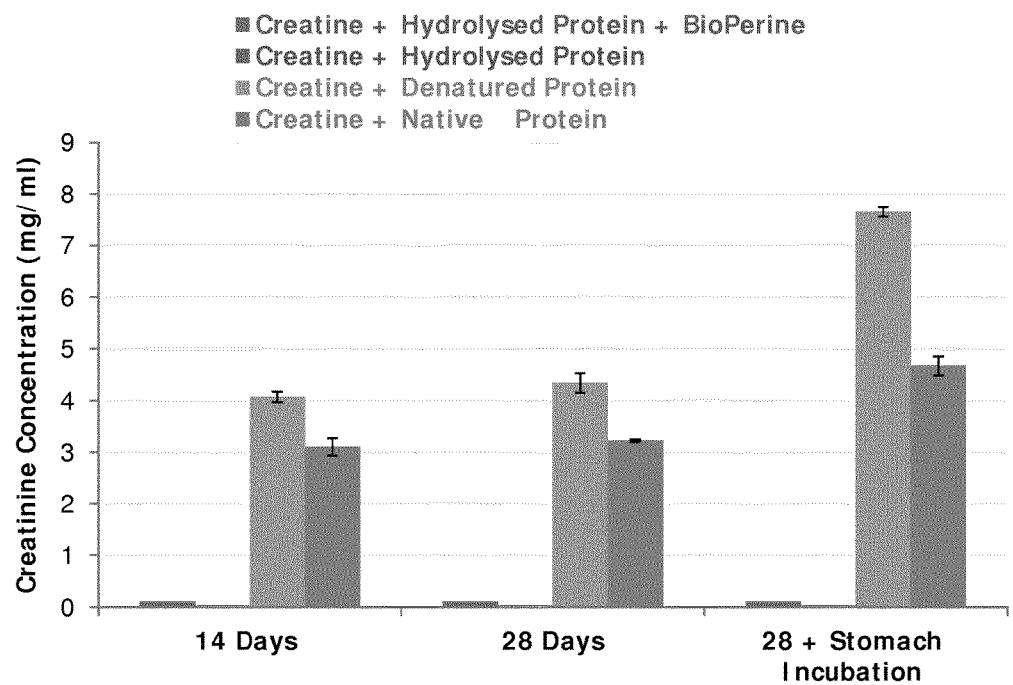
FIG. 10. Concentration of Creatinine during formation during 28-day storage in aqueous solution at pH 4.0 at room temperature. Treatments include hydrolysed milk protein capsules (■); hydrolysed milk protein capsules+BioPerine (■); native whey protein capsules (■) and Creatine in denatured whey protein capsules (■) at 25° C. for up to 28 days followed by exposure to ex vivo stomach contents (pH 1.6; 3 hours).

The critical factor for efficacious encapsulation of Creatine involves micro-particle adherence to the intestinal epithelium since adhesion ability is considered an important characteristics for rapid absorption of encapsulated material into the blood stream. This imperative selection criterion must be retained after intestinal liberation of encapsulated Creatine. Hence, this study evaluated the usefulness of whey protein micro-particles as suitable ex vivo delivery vehicles for delivery of active Creatine along the porcine gastro-intestinal tract with ileal tissue adhesion representing the indicator of rapid absorption into the blood stream. After 28 day storage in aqueous solution (pH 4.0) Creatine encapsulated in hydrolysed protein illustrated almost no loss in Creatine concentration. Furthermore, Creatinine was not detected at any significant levels after 28-day storage in hydrolysed milk protein encapsulation systems. FIG. 9 also illustrates that subsequent gastric incubation maintained complete Creatine concentration with no detection of Creatinine Creatine encapsulated in various forms of milk protein failed to express significant protective properties for Creatine after 28 day water storage as illustrated in FIG. 10. Therefore, native and denatured milk protein matrices expressed weak protective properties for Creatine and resulted in significant increases in Creatinine concentrations. Hence, hydrolysed whey protein encapsulation systems represent the only treatment capable of providing storage stability and acid tolerance to Creatine monohydrate during beverage storage and stomach incubation. Hydrolysed protein provides an encapsulation vehicle capable of maintaining maximum Creatine concentrations (8 mg/ml).

Absorption Capacity

Figure 11:
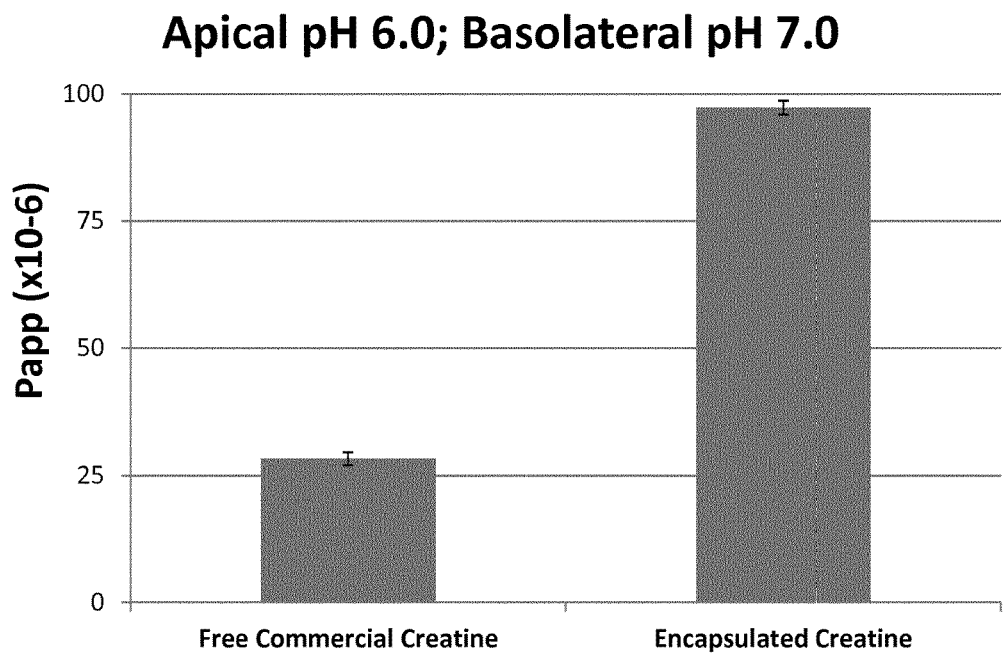
FIG. 11. Various levels of Creatine absorption were tested using standard absorption tests involving Caco-2 monolayers. Apical to basolateral permeability of free and encapsulated Creatine were tested and prepared to mimic in vivo conditions i.e. apical pH=6.0/basolateral pH=7.0).

Various levels of Creatine absorption were tested using standard absorption tests involving Caco-2 monolayers. Apical to basolateral permeability of free and encapsulated Creatine were tested and prepared to mimic in vivo conditions i.e. apical pH=6.0/basolateral pH=7.0). FIG. 11 shows that Creatine absorption was significantly enhanced as a result of electrostatic interaction with BioPerine. Electrophoretic mobility data demonstrated that free Creatine had a zeta potential of −2.4 mV compared to −23.14 mV for Creatine in the presence of BioPerine. Hence, creatine absorption was significantly enhanced as a result of the electrostatic interaction generated during the formation of the Creatine-BioPerine complex during the encapsulation process. As illustrated in FIG. 11, it is clear that absorption of encapsulated Creatine was highly dependent on molecular charge of Creatine i.e. encapsulated Creatine generated the substantial molecular charge in the presence of BioPerine at the pH utilised during encapsulation. Hence electrostatic potential of encapsulated Creatine provided sufficient i) aqueous solubility for Creatine solubility in fluids of the absorption site and ii) lipid solubility in the presence of BioPerine to allow sufficient partitioning of Creatine into lipoidal membranes and systemic circulation.

The invention is not limited to the embodiments herein before described which may be varied in construction and detail without departing from the spirit of the invention.

The invention claimed is:

1. A process for producing microencapsulates comprising an active component encapsulated within a polymerised hydrolysed protein matrix, the method comprising the steps of
   (a) providing a suspension comprising hydrolysed protein, an active component, and a liquid carboxylic ester,
   (b) extruding the suspension through a nozzle, thereby generating droplets of the suspension, and
   (c) immediately curing the droplets by immersion in a basic curing solution, wherein the liquid carboxylic ester in the suspension reacts with the basic curing solution to release a salt that polymerises the hydrolysed protein, thereby producing the microencapsulates.

2. The process of claim 1, wherein the hydrolysed protein is hydrolysed whey protein.

3. The process of claim 1, wherein the suspension additionally comprises pepper extract, wherein polymerisation of the hydrolysed protein encapsulates the active component and the pepper extract.

4. The process of claim 1, wherein the step of providing the suspension comprises mixing the active component, the hydrolysed protein, an organic carboxylic acid, and an alcohol, wherein the organic carboxylic acid and the alcohol react to form the liquid carboxylic ester.

5. The process of claim 1, wherein the basic curing solution comprises 0.01M-1.0M glycerol.

6. The process of claim 1, wherein the step of extruding the suspension to generate droplets employs a dual extrusion nozzle having a central nozzle and an outer nozzle, wherein the suspension is extruded through the central nozzle and a coating formulation comprising hydrolysed protein and a carboxylic ester is extruded through the outer nozzle to provide droplets having a core comprising the suspension and a coating comprising the coating formulation.

7. The process of claim 6, wherein the suspension is an emulsion and comprises an oil-soluble component.

8. The process of claim 7, wherein the oil-soluble component comprises astaxanthin that is optionally dissolved in a fatty acid.

9. The process of claim 1, wherein the active component is a pharmaceutically active agent.

10. The process of claim 1, wherein the active component comprises a creatine moiety, L-glutamine, L-leucine, beta-alanine, or a branched chain amino acid.

* * * * *